US011235051B2

(12) United States Patent
Vogels et al.

(10) Patent No.: US 11,235,051 B2
(45) Date of Patent: Feb. 1, 2022

(54) METHODS AND COMPOSITIONS FOR HETEROLOGOUS REPRNA IMMUNIZATIONS

(71) Applicants: Janssen Vaccines & Prevention B.V., Leiden (NL); Massachusetts Institute of Technology, Cambridge, MA (US)

(72) Inventors: Ronald Vogels, Linschoten (NL); Marijn Van Der Neut Kolfschoten, Amsterdam (NL); Darrell J. Irvine, Arlington, MA (US); Ron Weiss, Newton, MA (US); Ely Blanton Porter, Medford, MA (US); Mariane Bandeira Melo, Stoneham, MA (US); Tasuku Kitada, Ghent (BE)

(73) Assignees: Janssen Vaccines & Prevention B.V., Leiden (NL); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/634,205

(22) PCT Filed: Jul. 27, 2018

(86) PCT No.: PCT/US2018/044075
§ 371 (c)(1),
(2) Date: Jan. 27, 2020

(87) PCT Pub. No.: WO2019/023566
PCT Pub. Date: Jan. 31, 2019

(65) Prior Publication Data
US 2020/0230225 A1 Jul. 23, 2020

Related U.S. Application Data

(60) Provisional application No. 62/546,259, filed on Aug. 16, 2017, provisional application No. 62/538,070, filed on Jul. 28, 2017.

(51) Int. Cl.
| | | |
|---|---|---|
| A61K 48/00 | (2006.01) | |
| A61K 9/127 | (2006.01) | |
| C07K 14/535 | (2006.01) | |
| C12N 15/85 | (2006.01) | |
| A61K 31/7115 | (2006.01) | |
| A61K 39/12 | (2006.01) | |
| C12N 15/86 | (2006.01) | |
| A61K 39/00 | (2006.01) | |

(52) U.S. Cl.
CPC .............. *A61K 39/12* (2013.01); *C12N 15/86* (2013.01); *A61K 2039/53* (2013.01); *A61K 2039/545* (2013.01); *C12N 2760/18534* (2013.01)

(58) Field of Classification Search
CPC .. C07K 14/535; A61K 38/193; A61K 9/1271; A61K 48/0066; A61K 48/0033
See application file for complete search history.

(56) References Cited

U.S. PATENT DOCUMENTS

| | | | |
|---|---|---|---|
| 6,083,716 A | 7/2000 | Wilson et al. | |
| 7,270,811 B2 | 9/2007 | Bout et al. | |
| 2011/0300205 A1 | 12/2011 | Geall et al. | |
| 2013/0195968 A1 | 8/2013 | Geall et al. | |
| 2014/0271714 A1* | 9/2014 | Simmons | A61K 39/12 424/218.1 |

FOREIGN PATENT DOCUMENTS

| | | | |
|---|---|---|---|
| WO | 2003104467 | | 12/2003 |
| WO | 2004001032 | | 12/2003 |
| WO | 2005046621 | | 5/2005 |
| WO | WO2005046621 | * | 5/2005 |
| WO | 2005071093 | | 8/2005 |
| WO | 2007104792 | | 9/2007 |
| WO | 2010085984 | | 8/2010 |
| WO | 2010086189 | | 8/2010 |
| WO | 2012082918 | | 6/2012 |
| WO | 2013006842 | | 1/2013 |
| WO | 2016036971 | | 3/2016 |
| WO | WO2016036971 | * | 3/2016 |

OTHER PUBLICATIONS

Abbink et al., "Comparative seroprevalence and immunogenicity of six rare serotype recombinant adenovirus vaccine vectors from subgroups B and D," (2007) Virol 81(9): 4654-63.

Barefoot et al., "Comparison of multiple vaccine vectors in a single heterologous prime boost trial," 2008 Vaccine 26:6107-6118.

Bogers et al., "Potent Immune Responses in Rhesus Macaques Induced by Nonviral Delivery of a Self-amplifying RNA Vaccine Expressing HIV Type 1 Envelope With a Cationic Nanoemulsion," 2015, J Infect Dis., 211(6):947-55.

Cohen et al., "Chimpanzee adenovirus CV-68 adapted as a gene delivery vector interacts with the coxsackievirus and adenovirus receptor," 2002, J Gen Virol 83: 151-55.

Farina et al, "Replication-Defective Vector Based on a Chimpanzee Adenoviru," 2001, J Virol 75: 11603-13.

Fenoglio et al., "Generation of more effective cancer vaccines," 2013, Hum Vaccin Immunother, (12):2543-7.

Frolov et al. 1999, "Selection of RNA replicons capable of persistent noncytopathic replication in mammalian cells," J Virol., 73(5):3854-65.

(Continued)

*Primary Examiner* — Barry A Chestnut
(74) *Attorney, Agent, or Firm* — Ice Miller LLP

(57) ABSTRACT

Compositions and methods are described for inducing an immune response against an immunogen in humans. The induced immune response is obtained by administering a heterologous prime-boost combination of an in vitro transcribed (IVT) self-replicating RNA (repRNA) and an adenovirus vector. The compositions and methods can be used to provide a protective immunity against a disease, such as a viral infection or a cancer, in humans.

21 Claims, 8 Drawing Sheets
Specification includes a Sequence Listing.

(56) References Cited

OTHER PUBLICATIONS

Havenga et al., "Novel replication-incompetent adenoviral B-group vectors: high vector stability and yield in PER.C6 cells," 2006, J Gen Virol 87: 2135-43.

Kallen and Thess, "A development that may evolve into a revolution in medicine: mRNA as the basis for novel, nucleotide-based vaccines and drugs," 2014, Ther Adv Vaccines, 2(1) 10-31.

Kobinger et al., "Chimpanzee adenovirus vaccine protects against Zaire Ebola virus," 2006, Virology 346: 394-401.

Lee et al., "Venezuelan Equine Encephalitis Virus-Vectored Vaccines Protect Mice against Anthrax Spore Challenge," 2003 Infection and Immun. 71:1491-1496.

Ljungberg et al., "Self-replicating alphavirus RNA vaccines," Expert Revew of Vacc 14:177-194.

Naslund et al., "Comparative Prime-Boost Vaccinations Using Semliki Forest Virus, Adenovims, and ALVAC Vectors Demonstrate Differences in the Generation of a Protective Central Memory CTL Response against the P815 Tumor," 2007, J Immunol, 178:6761-6769.

Semple et al., "Rational design of cationic lipids for siRNA delivery," 2010, Nat Biotechnol. 28(2):172-176.

Sun et al., "Enhanced immunity against classical swine fever in pigs induced by prime-boost immunization using an alphavirus replicon-vectored DNA vaccine and a recombinant adenovirus," 2010 Vet Immunol Immunopathol. 137:20-27.

Tatsis et al., "A CD46-binding Chimpanzee Adenovirus Vector as a Vaccine Carrier," 2007, Molecular Therapy 15:608-17.

Vignuzzi et al., "Naked RNA immunization with replicons derived from poliovirus and Semliki Forest vims genomes for the generation of a cytotoxic T cell response against the influenza A virus nucleoprotein," 2001 J Gen Virol.82:1737-1747.

Vogel and Sarver N, "Nucleic acid vaccines," 1995, Clin Microbiol Rev., 8(3):406-10.

Vogels et al., "Replication-deficient human adenovirus type 35 vectors for gene transfer and vaccination: efficient human cell infection and bypass of preexisting adenovirus immunity," (2003) J Virol 77(15): 8263-71.

Zhao et al., "Prime-boost immunization using alphavirus replicon and adenovirus vectored vaccines induces enhanced immune responses against classical swine fever virus in mice," 2009 Vet Immun and Immunopathology 131:158-166.

International Search Report and Written Opinion issued Nov. 7, 2018 from International Application No. PCT/US2018/044075.

Alberer et al., "Safety and immunogenicity of a mRNA rabies vaccine in healthy adults: an open-label, non-randomised, prospective, first-in-human phase 1 clinical trial," The Lancet, published online Jul. 2017.

DeFrancesco et al., "The anti-hype vaccine", Nature Biotechnology, 35: 193-197.

International Preliminary Report on Patentability dated Feb. 6, 2020 from from International Application No. PCT/US2018/044075.

* cited by examiner

VEE-based repRNA construct

Figure 1

SEQUENCE LISTING

<160> NUMBER OF SEQ ID NOS: 3

<210> SEQ ID NO 1
<211> LENGTH: 574
<212> TYPE: PRT
<213> ORGANISM: Artificial Sequence
<220> FEATURE:
<223> OTHER INFORMATION: RSV-F protein, strain RSV-A2

<400> SEQUENCE: 1

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140
```

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
    515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

```
Lys Asp Gln Leu Ser Gly Ile Asn Asn Ile Ala Phe Ser Asn
            565                 570

<210> SEQ ID NO 2
<211> LENGTH: 574
<212> TYPE: PRT
<213> ORGANISM: Artificial Sequence
<220> FEATURE:
<223> OTHER INFORMATION: RSV-preF

<400> SEQUENCE: 2

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Gly Ala Leu
            35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

```
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
            450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
            485                 490                 495
Glu Lys Ile Asn Gln Ser Leu Ala Phe Ile Arg Lys Ser Asp Glu Leu
            500                 505                 510
Leu His Asn Val Asn Ala Val Lys Ser Thr Thr Asn Ile Met Ile Thr
            515                 520                 525
Thr Ile Ile Ile Val Ile Ile Val Ile Leu Leu Ser Leu Ile Ala Val
            530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
            565                 570
```

<210> SEQ ID NO 3
<211> LENGTH: 9676
<212> TYPE: DNA
<213> ORGANISM: Artificial Sequence
<220> FEATURE:
<223> OTHER INFORMATION: repRNA construct containing the RSV preF
    antigen

<400> SEQUENCE: 3

| | | |
|---|---|---|
| taatacgact cactatagat gggcggcgca tgagagaagc ccagaccaat acctaccca | 60 |
| aaatggagaa agttcacgtt gacatcgagg aagacagccc attcctcaga gctttgcagc | 120 |
| ggagcttccc gcagtttgag gtagaagcca agcaggtcac tgataatgac catgctaatg | 180 |
| ccagagcgtt ttcgcatctg gcttcaaaac tgatcgaaac ggaggtggac ccatccgaca | 240 |
| cgatccttga cattggaagt gcgcccgccc gcagaatgta ttctaagcac aagtatcatt | 300 |
| gtatctgtcc gatgagatgt gcggaagatc cggacagatt gtataagtat gcaactaagc | 360 |
| tgaagaaaaa ctgtaaggaa ataactgata aggaattgga caagaaaatg aaggagctcg | 420 |
| ccgccgtcat gagcgaccct gacctggaaa ctgagactat gtgcctccac gacgacgagt | 480 |
| cgtgtcgcta cgaagggcaa gtcgctgttt accaggatgt atacgcggtt gacgaccga | 540 |
| caagtctcta tcaccaagcc aataagggag ttagagtcgc ctactggata ggctttgaca | 600 |
| ccacccctt tatgtttaag aacttggctg agcatatcc atcatactct accaactggg | 660 |
| ccgacgaaac cgtgttaacg gctcgtaaca taggcctatg cagctctgac gttatggagc | 720 |
| ggtcacgtag agggatgtcc attcttagaa agaagtattt gaaaccatcc aacaatgttc | 780 |

```
tattctctgt tggctcgacc atctaccacg agaagaggga cttactgagg agctggcacc    840
tgccgtctgt atttcactta cgtggcaagc aaaattacac atgtcggtgt gagactatag    900
ttagttgcga cgggtacgtc gttaaaagaa tagctatcag tccaggcctg tatgggaagc    960
cttcaggcta tgctgctacg atgcaccgcg agggattctt gtgctgcaaa gtgacagaca   1020
cattgaacgg ggagagggtc tcttttcccg tgtgcacgta tgtgccagct acattgtgtg   1080
accaaatgac tggcatactg gcaacagatg tcagtgcgga cgacgcgcaa aaactgctgg   1140
ttgggctcaa ccagcgtata gtcgtcaacg gtcgcaccca gagaaacacc aataccatga   1200
aaaattacct tttgcccgta gtgcccagg catttgctag gtgggcaaag gaatataagg    1260
aagatcaaga agatgaaagg ccactaggac tacgagatag acagttagtc atggggtgtt   1320
gttgggcttt tagaaggcac aagataacat ctatttataa gcgcccggat acccaaacca   1380
tcatcaaagt gaacagcgat ttccactcat tcgtgctgcc caggataggc agtaacacat   1440
tggagatcgg gctgagaaca agaatcagga aaatgttaga ggagcacaag gagccgtcac   1500
ctctcattac cgccgaggac gtacaagaag ctaagtgcgc agccgatgag gctaaggagg   1560
tgcgtgaagc cgaggagttg cgcgcagctc taccacctt ggcagctgat gttgaggagc    1620
ccactctgga agccgatgtc gacttgatgt tacaagaggc tggggccggc tcagtggaga   1680
cacctcgtgg cttgataaag gttaccagct acgatggcga ggacaagatc ggctcttacg   1740
ctgtgctttc tccgcaggct gtactcaaga gtgaaaaatt atcttgcatc caccctctcg   1800
ctgaacaagt catagtgata acacactctg gccgaaaagg gcgttatgcc gtggaaccat   1860
accatggtaa agtagtggtg ccagagggac atgcaatacc cgtccaggac tttcaagctc   1920
tgagtgaaag tgccaccatt gtgtacaacg aacgtgagtt cgtaaacagg tacctgcacc   1980
atattgccac acatggagga gcgctgaaca ctgatgaaga atattacaaa actgtcaagc   2040
ccagcgagca cgacggcgaa tacctgtacg acatcgacag gaaacagtgc gtcaagaaag   2100
aactagtcac tgggctaggg ctcacaggcg agctggtgga tcctcccttc catgaattcg   2160
cctacgagag tctgagaaca cgaccagccg ctccttacca agtaccaacc atagggtgt    2220 atggcgtgcc aggatcaggc aagtctggca tcattaaaag cgcagtcacc aaaaaagatc   2280
tagtggtgag cgccaagaaa gaaaactgtg cagaaattat aagggacgtc aagaaaatga   2340
aagggctgga cgtcaatgcc agaactgtgg actcagtgct cttgaatgga tgcaaacacc   2400
ccgtagagac cctgtatatt gacgaagctt ttgcttgtca tgcaggtact ctcagagcgc   2460
tcatagccat tataagacct aaaaaggcag tgctctgcgg ggatcccaaa cagtgcggtt   2520 ttttttaacat gatgtgcctg aaagtgcatt ttaaccacga gatttgcaca caagtcttcc   2580
acaaaagcat ctctcgccgt tgcactaaat ctgtgacttc ggtcgtctca accttgtttt   2640
acgacaaaaa aatgagaacg acgaatccga aagagactaa gattgtgatt gacactaccg   2700
gcagtaccaa acctaagcag gacgatctca ttctcacttg tttcagaggg tgggtgaagc   2760
agttgcaaat agattacaaa ggcaacgaaa taatgacggc agctgcctct caagggctga   2820
cccgtaaagg tgtgtatgcc gttcggtaca aggtgaatga aaatcctctg tacgcaccca   2880
cctcagaaca tgtgaacgtc ctactgaccc gcacggagga ccgcatcgtg tggaaaacac   2940
tagccggcga cccatggata aaaacactga ctgccaagta ccctgggaat tcactgcca    3000 cgatagagga gtggcaagca gagcatgatg ccatcatgag gcacatcttg gagagaccgg   3060 acccctaccga cgtcttccag aataaggcaa acgtgtgttg ggccaaggct ttagtgccgg   3120
```

-continued

```
tgctgaagac cgctggcata gacatgacca ctgaacaatg gaacactgtg gattattttg    3180
aaacggacaa agctcactca gcagagatag tattgaacca actatgcgtg aggttctttg    3240
gactcgatct ggactccggt ctattttctg cacccactgt tccgttatcc attaggaata    3300
atcactggga taactcccg tcgcctaaca tgtacgggct gaataaagaa gtggtccgtc     3360
agctctctcg caggtaccca caactgcctc gggcagttgc cactggaaga gtctatgaca    3420
tgaacactgg tacactgcgc aattatgatc cgcgcataaa cctagtacct gtaaacagaa    3480
gactgcctca tgctttagtc ctccaccata atgaacaccc acagagtgac ttttcttcat    3540
tcgtcagcaa attgaagggc agaactgtcc tggtggtcgg ggaaaagttg tccgtcccag    3600
gcaaaatggt tgactggttg tcagaccggc ctgaggctac cttcagagct cggctggatt    3660
taggcatccc aggtgatgtg cccaaatatg acataatatt tgttaatgtg aggaccccat    3720
ataaatacca tcactatcag cagtgtgaag accatgccat taagcttagc atgttgacca    3780
agaaagcttg tctgcatctg aatcccggcg gaacctgtgt cagcataggt tatggttacg    3840
ctgacagggc cagcgaaagc atcattggtg ctatagcgcg gctgttcaag ttttcccggg    3900
tatgcaaacc gaaatcctca cttgaagaga cggaagttct gtttgtattc attgggtacg    3960
atcgcaaggc ccgtacgcac aatccttaca agctttcatc aaccttgacc aacatttata    4020
caggttccag actccacgaa gccggatgtg caccctcata tcatgtggtg cgaggggata    4080
ttgccacggc caccgaagga gtgattataa atgctgctaa cagcaaagga caacctggcg    4140
gaggggtgtg cggagcgctg tataagaaat cccggaaag cttcgattta cagccgatcg     4200
aagtaggaaa agcgcgactg gtcaaaggtg cagctaaaca tatcattcat gccgtaggac    4260
caaacttcaa caaagtttcg gaggttgaag gtgacaaaca gttggcagag cttatgagt     4320
ccatcgctaa gattgtcaac gataacaatt acaagtcagt agcgattcca ctgttgtcca    4380
ccggcatctt ttccgggaac aaagatcgac taacccaatc attgaaccat tgctgacag     4440
ctttagacac cactgatgca gatgtagcca tatactgcag ggacaagaaa tgggaaatga    4500
ctctcaagga agcagtggct aggagagaag cagtggagga gatatgcata tccgacgact    4560
cttcagtgac agaacctgat gcagagctgg tgagggtgca tccgaagagt tctttggctg    4620
gaaggaaggg ctacagcaca agcgatggca aaactttctc atatttggaa gggaccaagt    4680
ttcaccaggc ggccaaggat atagcagaaa ttaatgccat gtggcccgtt gcaacggagg    4740
ccaatgagca ggtatgcatg tatatcctcg agaaagcat gagcagtatt aggtcgaaat     4800
gccccgtcga agagtcggaa gcctccacac cacctagcac gctgccttgc ttgtgcatcc    4860
atgccatgac tccagaaaga gtacagcgcc taaaagcctc acgtccagaa caaattactg    4920
tgtgctcatc ctttccattg ccgaagtata gaatcactgg tgtgcagaag atccaatgct    4980
cccagcctat attgttctca ccgaaagtgc ctgcgtatat tcatccaagg aagtatctcg    5040
tggaaacacc accggtagac gagactccgg agccatcggc agagaaccaa tccacagagg    5100
ggacacctga acaaccacca cttataaccg aggatgagac caggactaga acgcctgagc    5160
cgatcatcat cgaagaggaa gaagaggata gcataagttt gctgtcagat ggcccgaccc    5220
accaggtgct gcaagtcgag gcagacattc acgggccgcc ctctgtatct agctcatcct    5280
ggtccattcc tcatgcatcc gactttgatg tggacagttt atccatactt gacacccctg    5340
agggagctag cgtgaccagc ggggcaacgt cagccgagac taactcttac ttcgcaaaga    5400
gtatggagtt tctggcgcga ccggtgcctg cgcctcgaac agtattcagg aaccctccac    5460
atccccgctcc gcgcacaaga acaccgtcac ttgcacccag cagggcctgc tcgagaacca    5520
```

```
gcctagtttc accccgcca ggcgtgaata gggtgatcac tagagaggag ctcgaggcgc   5580
ttaccccgtc acgcactcct agcaggtcgg tctcgagaac cagcctggtc tccaacccgc   5640
caggcgtaaa tagggtgatt acaagagagg agtttgaggc gttcgtagca caacaacaat   5700
gacggtttga tgcgggtgca tacatctttt cctccgacac cggtcaaggg catttacaac   5760
aaaaatcagt aaggcaaacg gtgctatccg aagtggtgtt ggagaggacc gaattggaga   5820
tttcgtatgc cccgcgcctc gaccaagaaa aagaagaatt actacgcaag aaattacagt   5880
taaatcccac acctgctaac agaagcagat accagtccag gaaggtggag aacatgaaag   5940
ccataacagc tagacgtatt ctgcaaggcc tagggcatta tttgaaggca gaaggaaaag   6000
tggagtgcta ccgaaccctg catcctgttc ctttgtattc atctagtgtg aaccgtgcct   6060
tttcaagccc caaggtcgca gtggaagcct gtaacgccat gttgaaagag aacttccga   6120 ctgtggcttc ttactgtatt attccagagt acgatgccta tttggacatg gttgacggag   6180
cttcatgctg cttagacact gccagttttt gccctgcaaa gctgcgcagc tttccaaaga   6240
aacactccta tttggaaccc acaatacgat cggcagtgcc ttcagcgatc cagaacacgc   6300
tccagaacgt cctggcagct gccacaaaaa gaaattgcaa tgtcacgcaa atgagagaat   6360
tgcccgtatt ggattcggcg gcctttaatg tggaatgctt caagaaatat gcgtgtaata   6420
atgaatattg ggaaacgttt aaagaaaacc ccatcaggct tactgaagaa aacgtggtaa   6480
attacattac caaattaaaa ggaccaaaag ctgctgctct ttttgcgaag acacataatt   6540
tgaatatgtt gcaggacata ccaatggaca ggtttgtaat ggacttaaag agagacgtga   6600
aagtgactcc aggaacaaaa catactgaag aacggcccaa ggtacaggtg atccaggctg   6660
ccgatccgct agcaacagcg tatctgtgcg gaatccaccg agagctggtt aggagattaa   6720
atgcggtcct gcttccgaac attcatacac tgtttgatat gtcggctgaa gactttgacg   6780
ctattatagc cgagcacttc cagcctgggg attgtgttct ggaaactgac atcgcgtcgt   6840
ttgataaaag tgaggacgac gccatggctc tgaccgcgtt aatgattctg gaagacttag   6900
gtgtggacgc agagctgttg acgctgattg aggcggcttt cggcgaaatt tcatcaatac   6960
atttgcccac taaaactaaa tttaaattcg gagccatgat gaaatctgga atgttcctca   7020
cactgtttgt gaacacagtc attaacattg taatcgcaag cagagtgttg agagaacggc   7080
taaccggatc accatgtgca gcattcattg gagatgacaa tatcgtgaaa ggagtcaaat   7140
cggacaaatt aatggcagac aggtgcgcca cctggttgaa tatggaagtc aagattatag   7200
atgctgtggt gggcgagaaa gcgccttatt tctgtggagg gtttattttg tgtgactccg   7260
tgaccggcac agcgtgccgt gtggcagacc ccctaaaaag gctgtttaag cttggcaaac   7320
ctctggcagc agacgatgaa catgatgatg acaggagaag ggcattgcat gaagagtcaa   7380
cacgctggaa ccgagtgggt attctttcag agctgtgcaa ggcagtagaa tcaaggtatg   7440
aaaccgtagg aacttccatc atagttatgg ccatgactac tctagctagc agtgttaaat   7500
cattcagcta cctgagaggg gcccctataa ctctctacgg ctaacctgaa tggactacga   7560
catagtctag tccgccaagg ccaccatgga actgctgatc ctgaaggcca acgccatcac   7620
caccatcctg accgccgtga ccttctgctt cgccagcggc cagaacatca ccgaggaatt   7680
ctaccagagc acctgtagcg ccgtgtccaa gggctacctg ggcgccctga gaaccggctg   7740
gtacaccagc gtgatcacca tcgagctgag caacatcaag gaaatcaagt gcaacggcac   7800
cgacgccaag gtcaagctga tcaagcagga actggacaag tacaagaacg ccgtgaccga   7860
```

```
gctgcagctg ctgatgcaga gcaccccgc caccaacaac cgggccagac gcgagctgcc    7920
ccggttcatg aactcacccc tgaacaacgc caaaaagacc aacgtgaccc tgagcaagaa    7980
gcggaagcgg cggttcctgg gcttcctgct gggcgtgggc agcgccattg cttctggcgt    8040
ggccgtgtct aaggtgctgc acctggaagg cgaagtgaac aagatcaaga gcgccctgct    8100
gagcaccaac aaggccgtgg tgtccctgag caacggcgtg tccgtgctga ccagcaaggt    8160
gctggatctg aagaactaca tcgacaagca gctgctgccc atcgtgaaca agcagagctg    8220
cagcatcccc aacatcgaga cagtgatcga gttccagcag aagaacaacc ggctgctgga    8280
aatcacccgc gagttcagcg tgaacgccgg cgtgaccacc cccgtgtcca cctacatgct    8340
gaccaacagc gagctgctga gcctgatcaa cgacatgccc atcaccaacg accagaaaaa    8400
gctgatgagc aacaacgtgc agatcgtgcg gcagcagagc tactccatca tgagcatcat    8460
caaagaagag gtgctggcct acgtggtgca gctgcccctg tacggcgtga tcgacacccc    8520
ctgctggaag ctgcacacca gcccctgtg caccaccaac accaaagagg gcagcaacat    8580
ctgcctgacc cggaccgacc ggggctggta ctgcgataat gccggctcag tctcattctt    8640
tccacaggcc gagacatgca aggtgcagag caaccgggtg ttctgcgaca ccatgaacag    8700
cctgaccctg ccctccgaag tgaacctgtg caacgtggac atcttcaacc ctaagtacga    8760
ctgcaagatc atgaccctcca agaccgacgt gtccagctcc gtgatcacct ccctgggcgc    8820
catcgtgtcc tgctacggca agaccaagtg caccgccagc aacaagaacc ggggcatcat    8880
caagaccttc agcaacggct gcgactacgt gtccaacaag ggggtggaca ccgtgtccgt    8940
gggcaacacc ctgtactacg tgaacaaaca ggaaggcaag agcctgtacg tgaagggcga    9000
gcccatcatc aacttctacg accccctggt gttccccagc gacgagttcg acgccagcat    9060
cagccaggtc aacgagaaga tcaaccgagc cctggccttc atcagaaaga gcgacgagct    9120
gctgcacaat gtgaatgccg tgaagtccac caccaatatc atgatcacca caatcatcat    9180
cgtgatcatc gtcatcctgc tgtccctgat cgccgtgggc ctgctgctgt actgcaaggc    9240
cagatccacc cctgtgaccc tgtccaagga ccagctgagc ggcatcaaca atatcgcctt    9300
ctccaactaa taatatgtta cgtgcaaagg tgattgtcac ccccgaaag accatattgt    9360 gacacaccct cagtatcacg cccaaacatt tacagccgcg gtgtcaaaaa ccgcgtggac    9420
gtggttaaca tccctgctgg gaggatcagc cgtaattatt ataattggct tggtgctggc    9480
tactattgtg gccatgtacg tgctgaccaa ccagaaacat aattgaatac agcagcaatt    9540
ggcaagctgc ttacatagaa ctcgcggcga ttggcatgcc gccttaaaat ttttatttta    9600
tttttctttt cttttccgaa tcggattttg tttttaatat ttcaaaaaaa aaaaaaaaaa    9660
aaaaaaaaaa aaaaaa                                                   9676
```

METHODS AND COMPOSITIONS FOR HETEROLOGOUS REPRNA IMMUNIZATIONS

CROSS-REFERENCE TO RELATED APPLICATION

This application is a Section 371 of International Application No. PCT/US2018/44075, filed Jul. 27, 2018, which was published in the English language on Jan. 31, 2019, under International Publication No. WO 2019/023566 A1, which claims the benefit of U.S. Provisional Application No. 62/546,259, filed Aug. 16, 2017, and U.S. Provisional Application No. 62/538,070, filed Jul. 28, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "sequence_listing", creation date of Jul. 26, 2017, and having a size of about 23,045 bytes. The sequence listing submitted concurrently via EFS-Web is part of the specification and is herein incorporated by reference in its entirety.

FIELD OF THE INVENTION

This invention relates to methods and compositions for inducing an immune response in a human subject. In particular, the induced immune response is obtained by administering a heterologous prime-boost combination of an in vitro transcribed (IVT) self-replicating RNA (repRNA) and an adenovirus vector. The methods and compositions provide a strong induction of humoral and cellular immune responses against an immunogen in a human subject, which can be used to provide an effective treatment and/or protection against a disease, such as a tumor or an infectious disease in the human subject.

BACKGROUND OF THE INVENTION

Vaccines can be used to provide immune protection against pathogens, such as viruses, bacteria, fungi, or protozoans, as well as cancers.

Infectious diseases are the second leading cause of death worldwide after cardiovascular disease but are the leading cause of death in infants and children (Lee and Nguyen, 2015, Immune Network, 15(2):51-7). Vaccination is the most efficient tool for preventing a variety of infectious diseases. The goal of vaccination is to generate a pathogen-specific immune response providing long-lasting protection against infection. Despite the significant success of vaccines, development of safe and strong vaccines is still required due to the emergence of new pathogens, re-emergence of old pathogens and suboptimal protection conferred by existing vaccines. Recent important emerging or re-emerging diseases include: severe acute respiratory syndrome (SARS) in 2003, the H1N1 influenza pandemic in 2009, and Ebola virus in 2014. As a result, there is a need for the development of new and effective vaccines against emerging diseases.

Cancer is one of the major killers in the Western world, with lung, breast, prostate, and colorectal cancers being the most common (Butterfield, 2015, BMJ, 350:h988). Several clinical approaches to cancer treatment are available, including surgery, chemotherapy, radiotherapy, and treatment with small molecule signaling pathway inhibitors. Each of these standard approaches has been shown to modulate antitumor immunity by increasing the expression of tumor antigens within the tumor or causing the release of antigens from dying tumor cells and by promoting anti-tumor immunity for therapeutic benefit. Immunotherapy is a promising field that offers alternative methods for treatment of cancer. Cancer vaccines are designed to promote tumor-specific immune responses, particularly cytotoxic CD8+ T cells that are specific to tumor antigens. Clinical efficacy must be improved in order for cancer vaccines to become a valid alternative or complement to traditional cancer treatments. Considerable efforts have been undertaken so far to better understand the fundamental requirements for clinically-effective cancer vaccines. Recent data emphasize that important requirements, among others, are (1) the use of multi-epitope immunogens, possibly deriving from different tumor antigens; (2) the selection of effective adjuvants; (3) the association of cancer vaccines with agents able to counteract the regulatory milieu present in the tumor microenvironment; and (4) the need to choose the definitive formulation and regimen of a vaccine after accurate preliminary tests comparing different antigen formulations (Fenoglio et al., 2013, Hum Vaccin Immunother, (12):2543-7). A new generation of cancer vaccines, provided with both immunological and clinical efficacy, is needed to address these requirements.

The potential of nucleic acid-based vaccines has been studied for many years (Vogel and Sarver N, 1995, Clin Microbiol Rev., 8(3):406-10). Clinical trials are currently being conducted using DNA-based vaccines or mRNA-based vaccines, including clinical trials of mRNA-based vaccines against viral targets, such as Rabies virus (see e.g., world wide web at clinicaltrials.gov; Alberer et al., The Lancet, published online July 2017, world wide web at dx.doi.org/10.1016/S0140-6736(17)31665-3; DeFrancesco et al., Nature Biotechnology, 35: 193-197).

A next generation of mRNA-based vaccines makes use of self-replicating RNA (repRNA), which is based on the self-replicating mechanism of positive-sense RNA viruses such as alphaviruses (see, e.g., Bogers et al., 2015, J Infect Dis., 211(6):947-55). Such repRNAs induce transient, high-level antigen expression in a broad range of tissues within a host, and are able to act in both dividing and non-dividing cells.

Alphaviruses belong to the Togaviridae family, and they have linear, single-stranded, positive-sense RNA genomes comprising two functional segments, each with their own promoter. The first segment, located at the 5' end of the genome, encodes nonstructural proteins that make up a self-assembling replicase that synthesizes the negative-strand RNA genome, the positive-strand RNA genome, and sub-genomic RNA. The second segment encodes the structural envelope and capsid proteins. Self-replicating RNAs (repRNAs), also referred to as alphavirus replicons, are nucleic acids derived from the full-length virus in which the genes encoding the structural proteins have been removed such that the replicon is capable of replicating within a cell but is unable to propagate as a virus. In the case of repRNA-based antigen expression systems, the genes encoding the antigens can be inserted downstream of the subgenomic promoter, in place of the genes encoding the structural proteins. RepRNAs can be delivered to a cell as a DNA molecule, from which a repRNA is launched, packaged in a viral replicon particle (VRP), or as a naked modified or unmodified RNA molecule.

The research on repRNA-based vaccines is still in preclinical phases, but clinical trials are expected to begin within a couple of years. Studies have shown that combining repRNA launched from DNA or packaged in a viral replicon particle (VRP) with adenovirus vectors in heterologous prime-boost vaccinations stimulates immune responses (see, e.g., WO2005046621; Zhao et al., 2009, Vet Immunol Immunopathol., 131:158-166; and Näslund et al., 2007, J Immunol, 178:6761-6769). In addition, it has been shown that humoral responses induced by a repRNA based vaccine can be boosted with a protein-based vaccine (Bogers et al., Id.).

However, heterologous vaccination using an adenovirus vector in combination with a DNA plasmid from which a repRNA is launched has several challenges. For example, DNA plasmids are associated with safety issues such as contaminations from bacterial production, risk of integration of DNA into the host genome and a lack of self-limiting expression of the antigens. On the other hand, a heterologous vaccination using an adenovirus vector in combination with repRNA launched from a VRP requires a packaging cell line to produce VRPs, which is a costly and time-consuming process with complex manufacturing challenges. Use of a protein-based vaccine in combination with a repRNA has the limitation that protein-based vaccines require costly and time-consuming cell-based production of the protein with the risk of contamination. In addition, most protein-based vaccines suffer from stability issues and require a cold-chain, and, in general, protein-based vaccines are limited to stimulation of humoral immune responses.

Accordingly, there is a need in the art for improved vaccines based on repRNA technology that can be used to induce protective humoral and cellular immunity against immunogens, especially when a fast response is required in case of a pandemic outbreak. Such vaccines would be cost-effective to produce and would have minimal adverse effects. They would further preferably be effective against a wide diversity of antigens.

BRIEF SUMMARY OF THE INVENTION

The invention satisfies this need by providing heterologous prime-boost immunization regimens using two different vaccine platforms, (i) in vitro transcribed (IVT) self-replicating mRNA (repRNA), and (ii) an adenovirus vector-based vaccine.

It has been found that problems associated with the use of DNA-based vaccines, VRP-packaged vaccines, and protein-based vaccines, some of which are discussed above, can be circumvented by the use of in vitro production of repRNA, which is a DNA-free product that can be produced by a fast, generic and cell-free production process (Kallen and Thess, 2014, Ther Adv Vaccines, 2(1) 10-31). The inventors unexpectedly found that combining IVT repRNA with an adenovirus vector in a heterologous prime-boost immunization regimen results in induced humoral and cellular immune responses that are stronger than those resulting from single or homologous prime-boost immunizations with adenovirus vector or IVT repRNA. The invention can therefore be used to generate highly potent vaccines against a broad range of targets.

In one general aspect, the invention relates to a method of inducing an immune response in a human subject by administering a heterologous prime-boost immunization comprising a combination of an IVT repRNA and an adenovirus vector.

In certain embodiments of the invention, heterologous prime-boost combinations of an IVT repRNA and an adenovirus vector generate an induced immune response to an antigenic protein or an immunogenic polypeptide thereof in a human subject. The antigenic protein or immunogenic polypeptide thereof can be any antigenic protein or immunogenic polypeptide thereof. For example, the antigenic protein or immunogenic polypeptide thereof can be derived from a pathogen, e.g., a virus, a bacterium, a fungus, a protozoan, or a cancer, e.g., a tumor.

Accordingly, one general aspect of the invention relates to a method of inducing an immune response in a human subject in need thereof, the method comprising:

a. administering to the human subject a first composition comprising an immunologically effective amount of an in vitro transcribed (IVT) self-replicating RNA (repRNA) comprising a first polynucleotide encoding a first antigenic protein or an immunogenic polypeptide thereof, together with a pharmaceutically acceptable carrier, and b. administering to the subject a second composition comprising an immunologically effective amount of an adenovirus vector comprising a second polynucleotide encoding a second antigenic protein or an immunogenic polypeptide thereof, together with a pharmaceutically acceptable carrier, wherein one of the compositions is a priming composition and the other composition is a boosting composition, to thereby obtain an induced immune response in the human subject, wherein the first and second antigenic proteins share at least one antigenic determinant.

Another general aspect of the invention relates to a combination for inducing an immune response in a human subject, comprising:

a. a first composition comprising an immunologically effective amount of an IVT repRNA comprising a first polynucleotide encoding a first antigenic protein or an immunogenic polypeptide thereof, together with a pharmaceutically acceptable carrier, and b. a second composition comprising an immunologically effective amount of an adenovirus vector comprising a second polynucleotide encoding a second antigenic protein or an immunogenic polypeptide thereof, together with a pharmaceutically acceptable carrier, wherein one of the compositions is administered to the human subject for priming the immune response and the other composition is administered to the human subject for boosting the immune response, wherein the first and second antigenic proteins share at least one antigenic determinant.

Another general aspect of the invention relates to use of a combination according to an embodiment of the invention for inducing an immune response in a human subject.

In preferred embodiments of the invention, the composition comprising the IVT repRNA is a priming composition and the composition comprising the adenovirus vector is a boosting composition.

In preferred embodiments of the invention, the induced immune response comprises an induced humoral, or antibody, immune response against the at least one antigenic determinant shared by the first and second antigenic proteins in the human subject. Such a response can, e.g., be characterized by the presence of a high proportion of responders, such as more than 50%, 60%, 70%, 80%, 90%, or 100% of subjects tested as determined by an enzyme-linked immunosorbent (ELISA) assay.

In preferred embodiments of the invention, the induced immune response comprises an induced cellular immune response against the at least one antigenic determinant shared by the first and second antigenic proteins in the human subject.

In one embodiment of the invention, the enhanced immune response generated by the method comprises an enhanced CD8+ T cell response against the at least one antigenic determinant shared by the first and second antigenic proteins in the human subject. Such a response can, e.g., be characterized by the presence of a high proportion of CD8+ responders, such as more than 50%, 60%, 70%, 80%, 90%, or 100% of subjects tested as determined by an enzyme-linked immunospot (ELISPOT) or an intracellular cytokine staining (ICS) assay. In another embodiment of the invention, the enhanced CD8+ T cell response generated by the method comprises an increase or induction of polyfunctional CD8+ T cells specific to the at least one antigenic determinant shared by the first and second antigenic proteins. Such polyfunctional CD8+ T cells express more than one cytokine, such as two or more of IFN-gamma, IL-2 and TNF-alpha.

In one embodiment of the invention, the enhanced immune response generated by the method comprises an enhanced CD4+ T cell response against the at least one antigenic determinant shared by the first and second antigenic proteins in the human subject. Such a response can, e.g., be characterized by the presence of a high proportion of CD4+ responders, such as more than 50%, 60%, 70%, 80%, 90%, or 100% of subjects tested as determined by an ELISPOT or an ICS assay. In another embodiment of the invention, the enhanced CD4+ T cell response generated by the method comprises an increase or induction of polyfunctional CD4+ T cells specific to the at least one antigenic determinant shared by the first and second antigenic proteins. Such polyfunctional CD4+ T cells express more than one cytokine, such as two or more of IFN-gamma, IL-2 and TNF-alpha.

In preferred embodiments of the invention, the induced immune response comprises an induced antibody response, an induced CD4+ T cell response, and an induced CD8+ T cell response, against the at least one antigenic determinant shared by the first and second antigenic proteins in the human subject.

In preferred embodiments, the IVT repRNA is a Venezuelan equine encephalitis (VEE) virus-based repRNA. In preferred embodiments, the IVT repRNA backbone is one of those described by Frolov et al. (1999, J Virol., 73(5):3854-65). In preferred embodiments, the IVT repRNA backbone is the backbone sequence of SEQ ID NO: 3 without the RSV pre-F protein insert.

In preferred embodiments, the adenovirus vector is a recombinant human adenovirus serotype 26 (Ad26) vector or a recombinant human adenovirus serotype 35 (Ad35) vector.

In embodiments of the invention, the boosting composition is administered 1-52 weeks after the priming composition is administered. In one embodiment of the invention, the boosting composition is administered 2-52 weeks after the priming composition is administered. In another embodiment of the invention, the boosting composition is administered 4-52 weeks after the priming composition is administered. In one embodiment of the invention, the boosting composition is administered 1 week after the priming composition is administered. In another embodiment of the invention, the boosting composition is administered 2 weeks after the priming composition is administered. In another embodiment of the invention, the boosting composition is administered 4 weeks after the priming composition is administered. In another embodiment of the invention, the boosting composition is administered. In another embodiment of the invention, the boosting composition is administered 8 weeks after the priming composition is administered. In further embodiments of the invention, the boosting composition is administered 6, 10, 12, 14, 16, 20, 24, or more weeks after the priming composition is administered.

In an embodiment of the invention, the first or second antigenic protein or immunogenic polypeptide thereof is derived from a pathogen, such as a virus, a bacterium, a fungus, or a protozoan. In preferred embodiments, the first or second antigenic protein or immunogenic polypeptide thereof is derived from a virus. In another embodiment of the invention, the antigenic protein is derived from a cancer. In preferred embodiments, the first or second antigenic protein or immunogenic polypeptide thereof is derived from a tumor.

In an embodiment of the invention, the first polynucleotide and the second polynucleotide encode for the same antigenic protein or immunogenic polypeptide thereof. In another embodiment of the invention, the first polynucleotide and the second polynucleotide encode for different immunogenic polypeptides or epitopes of the same antigenic protein. In yet another embodiment of the invention, the first polynucleotide and the second polynucleotide encode for different, but related, antigenic proteins or immunogenic polypeptide thereof. For example, the related antigenic proteins can be substantially similar proteins derived from the same antigenic protein, or different antigenic proteins derived from the same pathogen or tumor.

In preferred embodiments, the first and second antigenic proteins are identical or substantially identical.

In an embodiment of the invention, a method of the invention provides a protective immunity to the human subject against a disease associated with the antigenic protein, such as a tumor or an infectious disease. In one preferred embodiment, the prime-boost combination of IVT repRNA and adenovirus vector induces a protective immune response against a tumor in a human subject. In another preferred embodiment, the prime-boost combination of IVT repRNA and adenovirus vector induces an immune response against a pathogen in a human subject.

In preferred embodiments, the first or second antigenic protein is derived from a pre-fusion F protein from respiratory syncytial virus (RSV-preF), and the first and second antigenic proteins are identical or substantially identical.

In preferred embodiments, the first and second antigenic proteins each independently comprise an amino acid sequence selected from the group consisting of SEQ ID NO: 1, SEQ ID NO: 2, immunogenic polypeptides thereof, and combinations thereof.

In preferred embodiments, the IVT repRNA comprises a nucleic acid encoding an antigenic protein derived from an RSV-preF protein. Preferably, the IVT repRNA comprises a nucleic acid encoding an antigenic protein having the amino acid sequence of SEQ ID NO: 1, SEQ ID NO: 2, or an immunogenic polypeptide or antigenic determinant thereof. Most preferably, the IVT repRNA comprises the nucleic acid sequence of SEQ ID NO: 3.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 1 shows a schematic representation of a VEE virus-based repRNA encoding an RSV-preF protein;

DETAILED DESCRIPTION OF THE INVENTION

Figure 2:
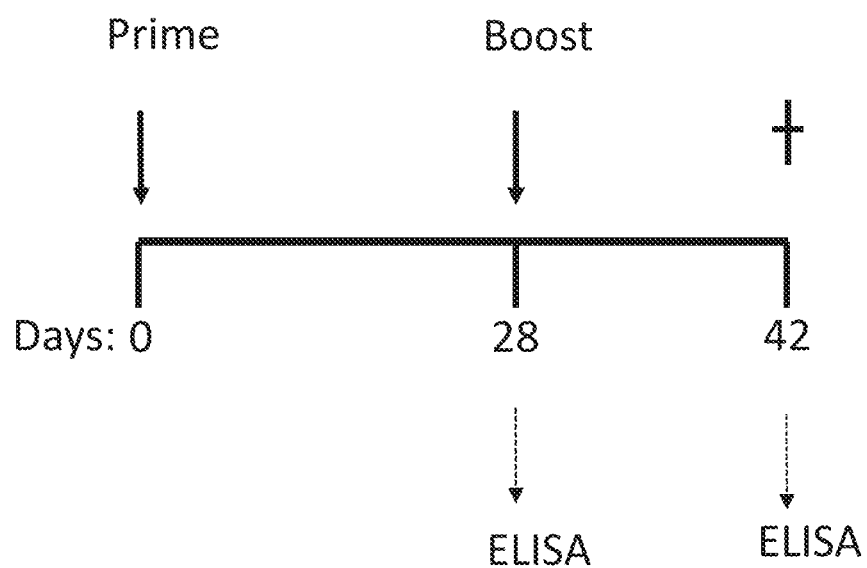
FIG. 2 shows an experimental design of a homologous IVT repRNA immunization study in which analysis was carried out by ELISA.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to whom will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

Protective immunity relies on both the innate and adaptive immune response. As used herein, the term "immune response" refers to the development in a subject of a humoral and/or cellular immunological response to an antigen that has been administered to the subject by the methods of the invention. "Humoral" immune responses refer to the production of antibodies by B cells, and a "cellular" immune response refers to the cytotoxic activity of CD8+ effector T cells and CD4+ T cells, also known as helper T cells. CD4+ T cells play a key role in both the humoral and the cellular immune response.

As used herein, the term "inducing" or "stimulating" and variations thereof refer to any measurable increase in cellular activity. Induction of an immune response can include, for example, activation, proliferation, or maturation of a population of immune cells, increasing the production of a cytokine, and/or another indicator of increased immune function. In certain embodiments, induction of an immune response can include increasing the proliferation of B cells, producing antigen-specific antibodies, increasing the proliferation of antigen-specific T cells, improving dendritic cell antigen presentation and/or an increasing expression of certain cytokines, chemokines and co-stimulatory markers.

As used herein, the term "induced antibody response" or "induced humoral immune response" refers to an antibody response in a human subject administered with a prime-boost combination of repRNA and adenovirus vector according to the invention, that is increased by a factor of at least 1.5, 2, 2.5, or more relative to the corresponding immune response observed from the human subject administered with a homologous prime-boost immunization of either repRNA or adenovirus vector alone at comparable dosages, using the same prime-boost regimen.

As used herein, the term "induced cellular immune response" refers to a cellular immune response in a human subject administered with a prime-boost combination of repRNA and adenovirus vector according to the invention, that is increased by a factor of at least 1.5, 2, 2.5, or more relative to the corresponding immune response observed from the human subject administered with a homologous prime-boost immunization of either repRNA or adenovirus vector alone at comparable dosages, using the same prime-boost regimen.

As used herein, the term "protective immunity" or "protective immune response" means that the vaccinated subject is able to control an infection or a disease related to an antigenic protein or immunogenic polypeptide thereof against which the vaccination was done. Usually, the subject having developed a protective immune response develops only mild to moderate clinical symptoms or no symptoms at all. Usually, a subject having a protective immune response or protective immunity against a certain antigenic protein will not die as a result of an infection or disease related to the antigenic protein.

As used herein, the term "immunologically effective amount" refers to an amount of an active ingredient or component that elicits the desired biological or medicinal response in a subject. An immunologically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

As used herein, the term "in vitro transcribed" refers to a method in which RNA is enzymatically synthesized in vitro in a cell-free manner, for example by using cell extracts or isolated enzymes.

As used herein, the term "self-replicating RNA," "self-replicating replicon RNA," or "repRNA" or "RNA replicon" refers to an RNA molecule expressing alphavirus nonstructural protein genes such that it can direct its own replication amplification in a cell, without producing a progeny virus. For example, a repRNA can comprise 5' and 3' alphavirus replication recognition sequences, coding sequences for alphavirus nonstructural proteins, a heterologous gene encoding an antigen and the means for expressing the antigen, and a polyadenylation tract. A repRNA of the invention can contain one or more mutations, such as attenuating mutations or mutations that improve functionality. A repRNA of the invention can contain modified nucleobases, such as those described in US2011/0300205, the relevant content of which is incorporated herein by reference. For example, the repRNAs of the invention can contain modified nucleosides including, but not limited to, m1G (1-methylguanosine), m2G (N2-methylguanosine), m7G (7-methylguanosine), Gm (2'-O-methylguanosine), m22G (N2,N2-dimethylguanosine), m2Gm (N2,2'-O-dimethylguanosine), and m22Gm (N2,N2,2'-O-trimethylguanosine.

As used herein, the term "antigenic protein" refers to a protein that is capable of stimulating an immune response in a vertebrate. As used herein, the term "immunogenic polypeptide thereof" or "immunogenic fragment thereof" refers to fragment of an antigenic protein that retains the capacity of stimulating an immune response. As used herein, the term "antigenic determinant" or "epitope" refers to the region of an antigenic protein that specifically reacts with an antibody.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an IVT repRNA-based or an adenovirus vector-based pharmaceutical composition can be used in the invention. Suitable excipients include but are not limited to sterile water, saline, dextrose, glycerol, ethanol, or the like and combinations thereof, as well as stabilizers, e.g. Human Serum Albumin (HSA) or other suitable proteins and reducing sugars.

As used herein, the term "priming composition", "priming immunization" or "prime immunization" refers to primary antigen stimulation by using a first composition of the invention. Specifically, the term "priming" or "potentiating" an immune response, as used herein, refers to a first immunization using an antigen which induces an immune response to the desired antigen and recalls a higher level of immune response to the desired antigen upon subsequent re-immunization with the same antigen. As used herein, the term "boosting composition", "boosting immunization" or "boost immunization" refers to an additional immunization administered to, or effective in, a mammal after the primary immunization. Specifically, the term "boosting" an immune response, as used herein, refers to the administration of a composition delivering the same antigen as encoded in the priming immunization.

As used herein, the term "pathogen" refers to an infectious agent such as a virus, a bacterium, a fungus, a parasite, or a prion that causes disease in its host.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using sequence comparison algorithms that are known and standard for those skilled in the art.

As used herein, the term "substantially identical" with respect to an antigen polypeptide sequence refers to an antigen polypeptide having at least 70%, preferably at least 80%, more preferably at least 90% and most preferably at least 95% sequence identity to the reference polypeptide sequence. The term "substantially identical" with respect to a nucleic acid sequence refers to a sequence of nucleotides having at least 70%, preferably at least 80%, more preferably at least 90% and most preferably at least 95% sequence identity to the reference nucleic acid sequence.

A further indication that two nucleic acid sequences or polypeptides are substantially identical is that the polypeptide encoded by the first nucleic acid is immunologically cross-reactive with the polypeptide encoded by the second nucleic acid. Thus, a polypeptide is typically substantially identical to a second polypeptide, for example, where the two peptides differ only by conservative substitutions.

Another indication that two nucleic acid sequences are substantially identical is that the two molecules hybridize to each other under stringent conditions.

It is discovered in the invention that heterologous prime-boost combinations, in particular, combinations of IVT repRNA and adenovirus vector, are surprisingly effective in generating protective immune responses in human subjects Antigenic Proteins Any DNA of interest can be inserted into the repRNA constructs and the adenovirus vectors described herein to be expressed heterologously from the repRNAs and vectors. Foreign genes for insertion into the genome of a virus in expressible form can be obtained using conventional techniques for isolating a desired gene in view of the present disclosure. For organisms, which contain a DNA genome, the genes encoding an antigen of interest can be isolated from the genomic DNA; for organisms with RNA genomes, the desired gene can be isolated from cDNA copies of the genome. The antigenic protein can also be encoded by a recombinant DNA that is modified based on a naturally occurring sequence, e.g., to optimize the antigenic response, gene expression, etc.

In certain embodiments of the invention, repRNA and adenovirus prime-boost combinations generate an induced immune response to an antigenic protein or an immunogenic polypeptide thereof in a human subject. The antigenic protein can be any antigenic protein related to an infection or disease.

According to embodiments of the invention, the antigenic protein or immunogenic polypeptide thereof can be isolated from, or derived from, a pathogen, such as a virus (e.g., filovirus, adenovirus, arbovirus, astrovirus, coronavirus, coxsackie virus, cytomegalovirus, Dengue virus, Epstein-Barr virus, hepatitis virus, herpesvirus, human immunodeficiency virus, human papilloma virus, human T-lymphotropic virus, influenza virus, JC virus, lymphocytic choriomeningitis virus, measles virus, molluscum contagiosum virus, mumps virus, norovirus, parovirus, poliovirus, rabies virus, respiratory syncytial virus, rhinovirus, rotavirus, rotavirus, rubella virus, smallpox virus, varicella zoster virus, West Nile virus, Zika virus, etc.), a bacteria (e.g., *Campylobacter jejuni*, *Escherichia coli*, *Helicobacter pylori*, *Mycobacterium tuberculosis*, *Neisseria gonorrhoeae*, *Neisseria meningitides*, *Salmonella*, *Shigella*, *Staphylococcus aureus*, *Streptococcus*, etc.), a fungus (e.g., *Coccidioides immitis*, *Blastomyces dermatitidis*, *Cryptococcus neoformans*, *Candida* species, *Aspergillus* species, etc.), a protozoan (e.g., *Plasmodium*, *Leishmania*, *Trypanosome*, *cryptosporidiums*, *Isospora*, *Naegleria fowleri*, *Acanthamoeba*, *Balamuthia mandrillaris*, *Toxoplasma gondii*, *Pneumocystis carinii*, etc.), or a cancer (e.g., bladder cancer, breast cancer, colon and rectal cancer, endometrial cancer, kidney cancer, leukemia, lung cancer, melanoma, non-Hodgkin lymphoma, pancreatic cancer, prostate cancer, thyroid cancer, etc.).

According to embodiments of the invention, the antigenic protein or immunogenic polypeptide thereof can be isolated from, or derived from, a tumor, such as a cancer.

In some embodiments, nucleic acids express antigenic domains rather than the entire antigenic protein. These fragments can be of any length sufficient to be immunogenic or antigenic. Fragments can be at least four amino acids long, preferably 8-20 amino acids, but can be longer, such as, e.g., 100, 200, 660, 800, 1000, 1200, 1600, 2000 amino acids long or more, or any length in between.

One of skill will recognize that the nucleic acid molecules encoding the antigenic protein can be modified, e.g., the nucleic acid molecules set forth herein can be mutated, as long as the modified expressed protein elicits an immune response against a pathogen or disease. Thus, as used herein, the term "antigenic protein" refers to a protein that comprises at least one antigenic determinant of a pathogen or a tumor described above. The term antigenic proteins also encompasses antigenic proteins that are substantially similar.

IVT RepRNAs

RepRNAs useful in the invention are derived from alphaviruses, which are single-strand positive-sense RNA viruses. In one embodiment, a RepRNA that can be used in the invention contains a 7methylguanosine cap, a 5' UTR, an RNA-dependent RNA polymerase (RdRp) polyprotein P1234 (i.e. nonstructural proteins, nsPs), a subgenomic promoter element, a variable region of interest from which an antigenic protein is expressed, a 3' UTR, and a poly(A) tail.

RepRNAs useful in the invention can be derived from any self-replicating positive strand RNA virus, for example RepRNAs can be derived from the virus families of Togaviridae or Arteriviridae, such as Aura virus, Babanki virus, Barmah Forest virus, Bebaru virus, Buggy Creek virus, Chikungunya virus, Eastern Equine Encephalitis virus, Everglades virus, Fort Morgan virus, Getah virus, Highlands J virus, Kyzylagach virus, Mayaro virus, Middleburg virus, Mucambo virus, Ndumu virus, O'nyong-nyong virus, Pixuna virus, Ross River virus, S.A. AR86, Sagiyama virus, Semliki Forest virus, Sindbis virus, Una virus, Venezuelan Equine Encephalitis virus, Western Equine Encephalitis virus, Whataroa virus, African pouched rat arterivirus, DeBrazza's monkey arterivirus, Equine arteritis virus, Kibale red colobus virus, Kibale red-tailed guenon virus, Lactate dehydrogenase-elevating virus, Mikumi yellow baboon virus 1, Pebjah virus, Porcine reproductive and respiratory syndrome virus. In preferred embodiments, repRNAs of the invention are derived from Venezuelan Equine Encephalitis (VEE) virus. Examples of preferred repRNA backbones of the invention include those described by Frolov et al., Id. and the backbone sequence of SEQ ID NO: 3 without the RSV pre-F protein insert.

The preparation of in vitro transcribed (IVT) RNA is well known in the art, and standard IVT and purification procedures can be used to prepare IVT repRNAs useful in the invention in view of the present disclosure.

Preparation of IVT repRNA is described, for example, in US2011/0300205 and US2013/0195968, the relevant content of which is incorporated herein by reference. For example, repRNA molecules can be prepared by IVT of a DNA that encodes the self-replicating RNA molecule using a suitable DNA-dependent RNA polymerase, such as T7 phage RNA polymerase, SP6 phage RNA polymerase, T3 phage RNA polymerase, etc. IVT can use a cDNA template created and propagated in plasmid from bacteria, or created synthetically, such as by gene synthesis and/or PCR-based methods. Appropriate capping addition reactions can be used as required, and the poly-A can be encoded within the DNA template or added by a poly-A reaction. Suitable synthetic methods can be used alone, or in combination with one or more other methods (e.g., recombinant DNA or RNA technology), to produce an IVT repRNA molecule of the invention. Suitable methods for de novo synthesis are well-known in the art and can be adapted for particular applications.

Typically, an IVT repRNA useful in the invention is produced using a DNA molecule from which the repRNA can be transcribed. Thus, the invention also provides isolated nucleic acid molecules that encode repRNAs of the invention. The nucleic acid molecules of the invention can be in the form of RNA or in the form of DNA obtained by cloning or produced synthetically. The DNA can be double-stranded or single-stranded.

IVT repRNAs useful in the invention can be formulated into suitable delivery systems for administration. In preferred embodiments, IVT repRNAs useful in the invention are formulated into non-virion particles for administration. Suitable non-virion particles are described, for example, in US2011/0300205 and US2013/0195968, the relevant content of which is incorporated herein by reference. For example, useful delivery systems include liposomes, polymer particles, non-toxic and biodegradable microparticles, electroporation, injection of naked RNA, and cationic submicron oil-in-water emulsions. In preferred embodiments, IVT repRNAs useful in the invention are formulated in lipid nanoparticle (LNP) compositions (see, e.g., Semple et al., 2010, Nat Biotechnol. 28(2):172-176, the relevant content of which is incorporated herein by reference).

As used herein, the term "lipid nanoparticle" or "LNP" refers to any lipid composition that can be used to deliver a therapeutic product, including, but not limited to, liposomes or vesicles, wherein an aqueous volume is encapsulated by amphipathic lipid bilayers, or wherein the lipids coat an interior that comprises a therapeutic product, or lipid aggregates or micelles, wherein the lipid-encapsulated therapeutic product is contained within a relatively disordered lipid mixture.

In particular embodiments, the LNPs comprise a cationic lipid to encapsulate and/or enhance the delivery of IVT repRNA into the target cell. The cationic lipid can be any lipid species that carries a net positive charge at a selected pH, such as physiological pH. The lipid nanoparticles can be prepared by including multi-component lipid mixtures of varying ratios employing one or more cationic lipids, non-cationic lipids and PEG-modified lipids. Several cationic lipids have been described in the literature, many of which are commercially available. For example, suitable cationic lipids for use in the compositions and methods of the invention include 1,2-dioleoyl-3-trimethylammonium-propane (DOTAP).

The LNP formulations can include anionic lipids. The anionic lipids can be any lipid species that carries a net negative charge at a selected pH, such as physiological pH. The anionic lipids, when combined with cationic lipids, are used to reduce the overall surface charge of LNPs and to introduce pH-dependent disruption of the LNP bilayer structure, facilitating nucleotide release. Several anionic lipids have been described in the literature, many of which are commercially available. For example, suitable anionic lipids for use in the compositions and methods of the invention include 1,2-dioleoyl-sn-glycero-3-phosphoethanolamine (DOPE).

LNPs can be prepared using methods well known in the art in view of the present disclosure. For example, the LNPs can be prepared using ethanol injection or dilution, thin film hydration, freeze-thaw, French press or membrane extrusion, diafiltration, sonication, detergent dialysis, ether infusion, and reverse phase evaporation. In preferred embodiments, LNPs useful in the invention are prepared by ethanol dilution.

Adenoviruses

An adenovirus according to the invention belongs to the family of the Adenoviridae and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV). In the invention, a human adenovirus is meant if referred to as Ad without indication of species, e.g. the brief notation "Ad26" means the same as HadV26, which is human adenovirus serotype 26. Also as used herein, the notation "rAd" means recombinant adenovirus, e.g., "rAd26" refers to recombinant human adenovirus 26.

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50. According to a particularly preferred embodiment of the invention, an adenovirus is a human adenovirus of one of the serotypes 26 or 35.

Advantages of these serotypes are a low seroprevalence and/or low pre-existing neutralizing antibody titers in the human population, and experience with use in human subjects in clinical trials.

Simian adenoviruses generally also have a low seroprevalence and/or low pre-existing neutralizing antibody titers in the human population, and a significant amount of work has been reported using chimpanzee adenovirus vectors (e.g. US6083716; WO 2005/071093; WO 2010/086189; WO 2010085984; Farina et al, 2001, J Virol 75: 11603-13; Cohen et al, 2002, J Gen Virol 83: 151-55; Kobinger et al, 2006, Virology 346: 394-401; Tatsis et al., 2007, Molecular Therapy 15: 608-17; see also review by Bangari and Mittal, 2006, Vaccine 24: 849-62; and review by Lasaro and Ertl, 2009, Mol Ther 17: 1333-39). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Adenoviral Vectors RAd26 and RAd35

In a preferred embodiment according to the invention the adenoviral vectors comprise capsid proteins from two rare serotypes: Ad26 and Ad35. In the typical embodiment, the vector is an rAd26 or rAd35 virus.

Thus, the vectors that can be used in the invention comprise an Ad26 or Ad35 capsid protein (e.g., a fiber, penton or hexon protein). One of skill will recognize that it is not necessary that an entire Ad26 or Ad35 capsid protein be used in the vectors of the invention. Thus, chimeric capsid proteins that include at least a part of an Ad26 or Ad35 capsid protein can be used in the vectors of the invention. The vectors of the invention can also comprise capsid proteins in which the fiber, penton, and hexon proteins are each derived from a different serotype, so long as at least one capsid protein is derived from Ad26 or Ad35. In preferred embodiments, the fiber, penton and hexon proteins are each derived from Ad26 or each from Ad35.

One of ordinary skill in the art will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of the Ad26 and Ad35 serotypes with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad35 or from Ad26 (i.e., the vector is rAd35 or rAd26). In some embodiments, the adenovirus is replication deficient, e.g. because it contains a deletion in the E1 region of the genome. For the adenoviruses of the invention, being derived from Ad26 or Ad35, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga et al, 2006, J Gen Virol 87: 2135-43; WO 03/104467). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E1B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al, 2006, supra; WO 2004/001032).

The preparation of recombinant adenoviral vectors is well known in the art.

Preparation of rAd26 vectors is described, for example, in WO 2007/104792 and in Abbink et al., (2007) Virol 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811 and in Vogels et al., (2003) J Virol 77(15): 8263-71. An exemplary genome sequence of Ad35 is found in GenBank Accession AC_000019.

In an embodiment of the invention, the vectors useful for the invention include those described in WO2012/082918, the disclosure of which is incorporated herein by reference in its entirety.

Typically, an adenovirus vector useful in the invention is produced using a nucleic acid comprising the entire recombinant adenoviral genome (e.g., a plasmid, cosmid, or baculovirus vector). Thus, the invention also provides isolated nucleic acid molecules that encode adenoviral vectors of the invention. The nucleic acid molecules of the invention can be obtained by cloning or produced synthetically. The DNA can be double-stranded or single-stranded.

The adenovirus vectors useful in the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention can contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6, 911, 293, and E1 A549.

In some embodiments, the adenovirus vector can express genes or portions of genes that encode antigenic peptides. These foreign, heterologous or exogenous peptides or polypeptides can include sequences that are immunogenic such as, for example, tumor-specific antigens (TSAs), bacterial, viral, fungal, and protozoal antigens.

The heterologous gene encoding an antigenic peptide can be under the control of (i.e., operably linked to) an adenovirus-derived promoter (e.g., the Major Late Promoter) or can be under the control of a heterologous promoter. Examples of suitable heterologous promoters include the CMV promoter and the RSV promoter. Preferably, the promoter is located upstream of the heterologous gene of interest within an expression cassette.

Immunogenic Compositions

Immunogenic compositions are compositions comprising an immunologically effective amount of repRNA or adenovirus vectors for use in the invention. The compositions can be formulated as vaccines (also referred to as "immunogenic compositions") according to methods well known in the art. Such compositions can include adjuvants to enhance immune responses. The optimal ratios of each component in the formulation can be determined by techniques well known to those skilled in the art in view of the present disclosure.

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

The compositions of the invention can comprise repRNA or adenovirus vectors expressing one or more antigenic proteins or immunogenic polypeptides thereof. These antigenic peptides or polypeptides can include any sequences that are immunogenic, including but not limited to, tumor-specific antigens (TSAs), bacterial, viral, fungal, and protozoal antigens. For example, the antigenic protein or immunogenic polypeptide thereof can be derived from a pathogen, e.g., a virus, a bacterium, a fungus, a protozoan, or it can also be derived from a tumor. In one or more preferred aspects, the compositions of the invention comprise repRNA or adenovirus vectors expressing one or more antigenic proteins from a virus, such as a respiratory syncytial virus (RSV, influenza virus, HIV, Ebola virus, HPV, HSV, CMV, RSV, Hepatitis virus, Zika virus, SARS virus, Chikungunys virus, Dengue virus, or West Nile virus.

The antigenic proteins can be any protein from any pneumovirus comprising an antigenic determinant. In a preferred embodiment the antigenic proteins are pre-fusion F protein from respiratory syncytial virus (RSV-preF).

In a preferred embodiment, the antigenic proteins encoded by the IVT repRNA or adenovirus vectors have the amino acid sequences of SEQ ID NO: 1, SEQ ID NO: 2, immunogenic polypeptides thereof, and combinations thereof.

The immunogenic compositions useful in the invention can comprise adjuvants.

Adjuvants suitable for co-administration in accordance with the invention should be ones that are potentially safe, well tolerated and effective in humans including QS-21, Detox-PC, MPL-SE, MoGM-CSF, TiterMax-G, CRL-1005, GERBU, TERamide, PSC97B, Adjumer, PG-026,GSK-I, GcMAF, B-alethine, MPC-026, Adjuvax, CpG ODN, Beta-fectin, Alum, and MF59.

Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-IO, and IL-12 or encoding nucleic acids therefore.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intravenous, cutaneous, intramucosal (e.g., gut), intranasal or intraperitoneal routes.

Method for Enhancing an Immune Response

The invention provides an improved method of priming and boosting an immune response to any antigenic protein or immunogenic polypeptide thereof in a human subject using an IVT repRNA in combination with an adenoviral vector.

According to one general aspect of the invention, a method of inducing an immune response in a human subject in need thereof comprises:

a. administering to the human subject a first composition comprising an immunologically effective amount of an in vitro transcribed (IVT) self-replicating RNA (repRNA) comprising a first polynucleotide encoding a first antigenic protein or an immunogenic polypeptide thereof, together with a pharmaceutically acceptable carrier, and b. administering to the subject a second composition comprising an immunologically effective amount of an adenovirus vector comprising a second polynucleotide encoding a second antigenic protein or an immunogenic polypeptide thereof, together with a pharmaceutically acceptable carrier, to thereby obtain an induced immune response in the human subject, wherein the first and second antigenic proteins share at least one antigenic determinant, and one of the compositions is a priming composition and the other composition is a boosting composition.

According to embodiments of the invention, the induced immune response comprises an induced antibody response against an antigenic protein in the human subject.

Preferably, the enhanced immune response further comprises an enhanced CD4+ response or an enhanced CD8+ T cell response against an antigenic protein in the human subject. The enhanced CD4+ T cell response generated by a method according to an embodiment of the invention can be, for example, an increase or induction of a dominant CD4+ T cell response against the antigenic protein, and/or an increase or induction of polyfunctional CD4+ T cells specific to the antigenic protein in the human subject. The polyfunctional CD4+ T cells express more than one cytokine, such as two or more of IFN-gamma, IL-2 and TNF-alpha. The enhanced CD8+ T cell response generated by a method according to an embodiment of the invention can be, for example, an increase or induction of polyfunctional CD8+ T cells specific to the antigenic protein in the human subject.

More preferably, the enhanced immune response resulting from a method according to an embodiment of the invention comprises an enhanced CD4+ T cell response, an enhanced antibody response and an enhanced CD8+ T cell response, against the antigenic protein in the human subject.

Assays that can be used to detect immune responses are well known in the art. Some of such assays include, e.g., ELISA (enzyme-linked immunosorbent assay), ELISPOT (enzyme-linked immunospot), and ICS (intracellular cytokine staining). ELISA assays analyze, e.g., levels of secreted antibodies or cytokines. When ELISA assays are used to determine levels of antibodies that bind to a particular antigen, an indicator of the humoral immune response, they can also reflect CD4+ T cell activity, as the production of high-affinity antibodies by B cells depends on the activity of CD4+ helper T cells. ELISPOT and ICS are single-cell assays that analyze, e.g., T cell responses to a particular antigen. ELISPOT assays measure the secretory activity of individual cells, and ICS assays analyze levels of intracellular cytokine. CD4+ specific and CD8+ specific T cell responses can be determined using ICS assays.

In one or more embodiments of the invention, an IVT repRNA is used to prime the immune response, and an Ad26 or Ad35 vector is used to boost the immune response according to an embodiment of the invention. In other embodiments of the invention, an Ad26 or Ad35 vector is used to prime the immune response, and an IVT repRNA is used to boost the immune response according to an embodiment of the invention.

The antigens in the priming and boosting compositions need not to be identical, but should share antigenic determinants or be substantially similar to each other.

Administration of the immunogenic compositions is typically intramuscular, subcutaneous or intradermal. However, other modes of administration such as intravenous, cutaneous or intranasal can be used as well. Intramuscular administration of the immunogenic compositions can be achieved by using a needle to inject a suspension of the composition. An alternative is the use of a needleless injection device to administer the composition (using, e.g., Biojector™) or a freeze-dried powder containing the composition.

For intravenous, cutaneous or subcutaneous injection, or injection at the site of affliction, the composition will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. IVT repRNAs of the invention can be formulated in lipid nanoparticles for administration. Preservatives, stabilizers, buffers, antioxidants and/or other additives can be included in the compositions, as required. A slow-release formulation of the compositions can also be employed.

Typically, administration will have a prophylactic aim to generate an immune response against an antigen before infection or development of symptoms. Diseases and disorders that can be treated or prevented in accordance with the invention include those in which an immune response can play a protective or therapeutic role. In other embodiments, the IVT repRNA and adenovirus vector can be administered for post-exposure prophylactics.

The immunogenic compositions containing the IVT repRNA and the adenovirus vector are administered to a subject, giving rise to an immune response in the subject. An amount of a composition sufficient to in induce a detectable immune response is defined to be an "immunologically effective dose." As shown below, the immunogenic compositions of the invention induce a humoral as well as a cell-mediated immune response. In a preferred embodiment the immune response is a protective immune response.

The actual amount of the compositions administered, and the rate and time-course of administration, will depend on the nature and severity of the disease, disorder or condition being treated. Prescription of treatment, e.g., decisions on dosage etc., is within the responsibility of general practitioners and other medical doctors, and typically takes account of the disease, disorder or condition to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of IVT repRNA and adenovirus vectors and optional formulation of such particles into compositions, the composition can be administered to an individual, particularly a human.

The therapeutically effective amount or dosage can vary according to various factors, such as the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

In one exemplary regimen, the IVT repRNA is administered (e.g., intramuscularly) in a volume ranging between about 100 µl to about 10 ml containing a dose of ≤200 µg, ≤100 µg, ≤50 µg, or ≤10 µg IVT repRNA, but expression can be seen at much lower levels, e.g. ≤1 µg, ≤100 ng, ≤10 ng, or ≤1 ng IVT repRNA per dose. Preferably, the IVT repRNA is administered in a volume ranging between 0.25 ml and 1.0 ml. More preferably the IVT repRNA is administered in a volume of 0.5 ml.

Typically, the IVT repRNA is administered in an amount of about 10-100 µg per dose. In a preferred embodiment, the IVT repRNA is administered in an about of about 10 µg per dose. In another preferred embodiment, the IVT repRNA is administered in an about of about 25 µg per dose. In another preferred embodiment, the IVT repRNA is administered in an about of about 50 µg per dose. In another preferred embodiment, the IVT repRNA is administered in an about of about 75 µg per dose. In another preferred embodiment, the IVT repRNA is administered in an about of about 100 µg per dose.

In one exemplary regimen, the adenovirus vector is administered (e.g., intramuscularly) in a volume ranging between about 100 µl to about 10 ml containing concentrations of about $10^4$ to $10^{12}$ virus particles/ml. Preferably, the adenovirus vector is administered in a volume ranging between 0.25 ml and 1.0 ml. More preferably the adenovirus vector is administered in a volume of 0.5 ml.

Typically, the adenovirus is administered in an amount of about $10^9$ to about $10^{12}$ viral particles (vp) to a human subject during one administration, more typically in an amount of about $10^{10}$ to about $10^{12}$ vp. In a preferred embodiment, the adenovirus vector is administered in an amount of about $5\times10^{10}$ vp. In another preferred embodiment, the adenovirus vector is administered in an amount of about $0.8\times10^{10}$ vp. In another preferred embodiment, the adenovirus vector is administered in an amount of about $2\times10^{10}$ vp. In another preferred embodiment, the adenovirus vector is administered in an amount of about $4\times10^{10}$ vp.

The compositions of the invention can be administered alone or in combination with other treatments, either simultaneously or sequentially dependent upon the condition to be treated.

Boosting compositions are administered weeks or months after administration of the priming composition, for example, about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or one to two years after administration of the priming composition.

Preferably, the boosting composition is administered 1-52 weeks after the priming composition is administered. In a preferred embodiment of the invention, the boosting composition is administered 2-52 weeks after the priming composition is administered. In another preferred embodiment of the invention, the boosting composition is administered 4-52 weeks after the priming composition is administered. In another preferred embodiment of the invention, the boosting composition is administered 1 week after the priming composition is administered. In another preferred embodiment of the invention, the boosting composition is administered 2 weeks after the priming composition is administered. In another preferred embodiment of the invention, the boosting composition is administered 4 weeks after the priming composition is administered. In another preferred embodiment of the invention, the boosting composition is administered 8 weeks after the priming composition is administered.

The priming and boosting compositions of the invention can each comprise one, two, three or multiple doses.

In one embodiment, the invention relates to a method of inducing an immune response against a tumor in a human subject. The method comprises:

a. administering to the human subject a first composition comprising an immunologically effective amount of an IVT repRNA comprising a first polynucleotide encoding an antigenic protein produced by a cell of the tumor, a substantially similar antigenic protein, or an immunogenic polypeptide thereof, together with a pharmaceutically acceptable carrier, and b. administering to the subject a second composition comprising an immunologically effective amount of an adenovirus vector comprising a second polynucleotide encoding the antigenic protein, the substantially similar antigenic protein, or an immunogenic polypeptide thereof, together with a pharmaceutically acceptable carrier, to thereby obtain an induced immune response against the tumor in the human subject, wherein the first and second antigenic proteins share at least one antigenic determinant, and one of the compositions is a priming composition and the other composition is a boosting composition.

Preferably, the induced immune response provides the human subject with a protective immunity against the tumor.

In a preferred embodiment, the composition comprising the IVT repRNA is the priming composition and the composition comprising the adenovirus vector is the boosting composition.

According to embodiments of the invention, the boosting composition is administered 1-52 weeks after the priming composition is administered. The boosting composition can also be administered later than 52 weeks after the priming composition is administered.

In one embodiment of the invention, the boosting composition is administered 2-52 weeks after the priming composition is administered. In another embodiment of the invention, the boosting composition is administered 4-52 weeks after the priming composition is administered. In another embodiment of the invention, the boosting composition is administered 1 week after the priming composition is administered. In another embodiment of the invention, the boosting composition is administered 2 weeks after the priming composition is administered. In another embodiment of the invention, the boosting composition is administered 4 weeks after the priming composition is administered. In another embodiment of the invention, the boosting composition is administered 8 weeks after the priming composition is administered.

In additional embodiments, the boosting composition is administered at least 2 weeks or at least 4 weeks after the priming composition is administered. In still other embodiments, the boosting composition is administered 4-12 weeks or 4-8 weeks after the priming composition is administered.

In a preferred embodiment, the IVT repRNA is a VEE virus-based repRNA.

In a preferred embodiment, the adenovirus vector is an Ad26 or an Ad35 vector.

The antigenic protein produced by a cell of the tumor can be any tumor antigen. In a preferred embodiment, the tumor antigen is a tumor-specific antigen that is present only on tumor cells. The tumor antigen can also be a tumor-associated antigen that is present on some tumor cells and also some normal cells.

According to another embodiment, the invention relates to a method of inducing an immune response against a virus in a human subject. The method comprises:

a. administering to the human subject a first composition comprising an immunologically effective amount of an IVT repRNA comprising a first polynucleotide encoding an antigenic protein of the virus, a substantially similar antigenic protein, or an immunogenic polypeptide thereof, together with a pharmaceutically acceptable carrier, and b. administering to the subject a second composition comprising an immunologically effective amount of an adenovirus vector comprising a second polynucleotide encoding the antigenic protein, the substantially similar antigenic protein, or an immunogenic polypeptide thereof, together with a pharmaceutically acceptable carrier, to thereby obtain an induced immune response against the virus in the human subject, wherein the first and second antigenic proteins share at least one antigenic determinant, and one of the compositions is a priming composition and the other composition is a boosting composition.

Preferably, the enhanced immune response provides the human subject a protective immunity against the virus.

In a preferred embodiment, the composition comprising the IVT repRNA is the priming composition and the composition comprising the adenovirus vector is the boosting composition.

In one embodiment, the boosting composition is administered 1-52 weeks after the priming composition is administered. The boosting composition can also be administered later than 52 weeks after the priming composition is administered.

In another embodiment of the invention, the boosting composition is administered 2-52 weeks after the priming composition is administered. In another embodiment of the invention, the boosting composition is administered 4-52 weeks after the priming composition is administered. In another embodiment of the invention, the boosting composition is administered 1 week after the priming composition is administered. In another embodiment of the invention, the boosting composition is administered 2 weeks after the priming composition is administered. In another embodiment of the invention, the boosting composition is administered 4 weeks after the priming composition is administered. In another embodiment of the invention, the boosting composition is administered 8 weeks after the priming composition is administered.

In additional embodiments, the boosting composition is administered at least 2 weeks or at least 4 weeks after the priming composition is administered. In still other embodiments, the boosting composition is administered 4-12 weeks or 4-8 weeks after the priming composition is administered.

In a preferred embodiment, the IVT repRNA is a VEE virus-based repRNA.

In a preferred embodiment, the adenovirus vector is an Ad26 or an Ad35 vector.

The antigenic protein can be any antigenic protein of a virus. In a preferred embodiment, the antigenic protein is a glycoprotein or a nucleoprotein of a virus.

EMBODIMENTS

The invention provides also the following non-limiting embodiments.

Embodiment 1 is a method of inducing an immune response in a human subject in need thereof, the method comprising:

a. administering to the human subject a first composition comprising an immunologically effective amount of an in vitro transcribed (IVT) self-replicating RNA (repRNA) comprising a first polynucleotide encoding a first antigenic protein or an immunogenic polypeptide thereof, together with a pharmaceutically acceptable carrier, and b. administering to the subject a second composition comprising an immunologically effective amount of an adenovirus vector comprising a second polynucleotide encoding a second antigenic protein or an immunogenic polypeptide thereof, together with a pharmaceutically acceptable carrier,
to thereby obtain an induced immune response in the human subject, wherein the first and second antigenic proteins share at least one antigenic determinant, and one of the compositions is a priming composition and the other composition is a boosting composition.

Embodiment 2 is the method according to Embodiment 1, wherein the composition comprising the IVT repRNA is the priming composition and the composition comprising the adenovirus vector is the boosting composition.

Embodiment 3 is the method according to Embodiment 1, wherein the composition comprising the adenovirus vector is the priming composition and the composition comprising the IVT repRNA is the boosting composition.

Embodiment 4 is the method according to any one of Embodiments 1 to 3, wherein the induced immune response comprises an induced antibody immune response against the at least one antigenic determinant shared by the first and second antigenic proteins in the human subject.

Embodiment 5 is the method according to Embodiment 4, wherein the induced antibody immune response is determined by an ELISA.

Embodiment 6 is the method according to any one of Embodiments 1 to 3, wherein the induced immune response comprises an induced cellular immune response against the at least one antigenic determinant shared by the first and second antigenic proteins in the human subject.

Embodiment 7 is the method according to Embodiment 6, wherein the induced cellular immune response is determined by an ICS or an ELISPOT assay.

Embodiment 8 is the method according to any one of Embodiments 1 to 7, wherein the induced immune response provides a protective immunity to the human subject against a disease related to at least one of the first and second antigenic proteins.

Embodiment 9 is the method according to any one of Embodiments 1 to 8, wherein the IVT repRNA is a Venezuelan equine encephalitis (VEE) virus-based repRNA.

Embodiment 10 is the method according to any one of Embodiments 1 to 9, wherein the adenovirus vector is a recombinant human adenovirus serotype 26 (Ad26) vector or a recombinant human adenovirus serotype 35 (Ad35) vector.

Embodiment 11 is the method according to any one of Embodiments 1 to 10, wherein the boosting composition is administered 1-52 weeks after the priming composition is administered.

Embodiment 12 is the method according to any one of Embodiments 1 to 11, wherein the boosting composition is administered at least 1 week after the priming composition is administered.

Embodiment 13 is the method according to any one of Embodiments 1 to 12, wherein the first or second antigenic protein is derived from a pathogen or a tumor.

Embodiment 14 is the method according to any one of Embodiments 1 to 12, wherein the first or second antigenic protein is derived from a virus.

Embodiment 15 is the method according to Embodiment 14, wherein the first or second antigenic protein is derived from a pneumovirus virus, Filovirus, HIV, Dengue virus, Zika virus, Influenza virus or hepatitis B virus.

Embodiment 16 is the method according to any one of Embodiments 1 to 15, wherein the first and second antigenic proteins are identical or substantially identical.

Embodiment 17 is the method according to any one of Embodiments 1 to 16, wherein the first or second antigenic protein is derived from a pre-fusion F protein from respiratory syncytial virus (RSV-preF), and wherein the first and second antigenic proteins are identical or substantially identical.

Embodiment 18 is the method according to Embodiment 17, wherein the first and second antigenic proteins each independently comprise an amino acid sequence selected from the group consisting of SEQ ID NO: 1, SEQ ID NO: 2, immunogenic polypeptides thereof, and combinations thereof.

Embodiment 19 is the method according to Embodiment 18, wherein the IVT repRNA comprises a polynucleotide encoding at least one antigenic protein having an amino acid sequence selected from the group consisting of SEQ ID NO: 1, SEQ ID NO: 2, and immunogenic polypeptides thereof.

Embodiment 20 is the method according to Embodiment 21, wherein the IVT repRNA comprises a polynucleotide having the sequence of SEQ ID NO: 3.

Embodiment 21 is the method according to Embodiment 20, wherein the adenovirus vector comprises a polynucleotide encoding at least one antigenic protein having an amino acid sequence selected from the group consisting of SEQ ID NO: 1, SEQ ID NO: 2, and immunogenic polypeptides thereof.

Embodiment 22 is the method according to any one of Embodiments 1 to 21, wherein the IVT repRNA is administered as a lipid nanoparticle composition at an amount of 0.1-1000 µg IVT repRNA per dose.

Embodiment 23 is the method according to any one of Embodiments 1 to 22, wherein the adenovirus vector is administered in an amount of $10^9$-$10^{12}$ viral particles per dose.

Embodiment 24 is a method of inducing an immune response against at least one pneumovirus subtype in a human subject, comprising:
a. administering to the human subject a first composition comprising an immunologically effective amount of an IVT repRNA comprising a first polynucleotide encoding a first antigenic protein of the at least one pneumovirus subtype, or an immunogenic polypeptide thereof, together with a pharmaceutically acceptable carrier, and
b. administering to the subject a second composition comprising an immunologically effective amount of an adenovirus vector comprising a second polynucleotide encoding a second antigenic protein of the at least one pneumovirus subtype, or an immunogenic polypeptide thereof, together with a pharmaceutically acceptable carrier,
to thereby obtain an induced immune response against the at least one pneumovirus subtype in the human subject, wherein the first and second antigenic proteins share at least one antigenic determinant, and one of the compositions is a priming composition and the other composition is a boosting composition.

Embodiment 25 is a combination for inducing an immune response in a human subject, comprising:
a. a first composition comprising an immunologically effective amount of an IVT repRNA comprising a first polynucleotide encoding a first antigenic protein or an immunogenic polypeptide thereof, together with a pharmaceutically acceptable carrier, and
b. a second composition comprising an immunologically effective amount of an adenovirus vector comprising a second polynucleotide encoding a second antigenic protein or an immunogenic polypeptide thereof, together with a pharmaceutically acceptable carrier, wherein one of the compositions is administered to the human subject for priming the immune response and the other composition is administered to the human subject for boosting the immune response,
wherein the first and second antigenic proteins share at least one antigenic determinant.

Embodiment 26 is a use of a combination for the preparation of a medicament for inducing an immune response in a human subject, comprising:
  a. a first composition comprising an immunologically effective amount of an IVT repRNA comprising a first polynucleotide encoding a first antigenic protein or an immunogenic polypeptide thereof, together with a pharmaceutically acceptable carrier, and
  b. a second composition comprising an immunologically effective amount of an adenovirus vector comprising a second polynucleotide encoding a second antigenic protein or an immunogenic polypeptide thereof, together with a pharmaceutically acceptable carrier, wherein one of the compositions is administered to the human subject for priming the immune response and the other composition is administered to the human subject for boosting the immune response,
wherein the first and second antigenic proteins share at least one antigenic determinant.

Embodiment 27 is the method of Embodiment 24, combination of Embodiment 25 or use of Embodiment 26, wherein the composition comprising the IVT repRNA is the priming composition and the composition comprising the adenovirus vector is the boosting composition.

Embodiment 28 is the method of Embodiment 24, combination of Embodiment 25 or use of Embodiment 26, wherein the composition comprising the adenovirus vector is the priming composition and the composition comprising the IVT repRNA is the boosting composition.

Embodiment 29 is the method of Embodiment 24, combination of Embodiment 25 or use of Embodiment 26, wherein the first or second antigenic protein or immunogenic polypeptide thereof is derived from a pathogen or a tumor.

Embodiment 30 is the method of Embodiment 24, combination of Embodiment 25 or use of Embodiment 26, wherein the first or second antigenic protein or immunogenic polypeptide thereof is derived from a virus.

Embodiment 31 is the method of Embodiment 24, combination of Embodiment 25 or use of Embodiment 26, wherein the first or second antigenic protein is derived from a RSV-preF protein, and wherein the first and second antigenic proteins are identical or substantially identical.

Embodiment 32 is the method of Embodiment 24, combination of Embodiment 25 or use of Embodiment 26, wherein the first and second antigenic proteins each independently comprise an amino acid sequence selected from the group consisting of SEQ ID NO: 1, SEQ ID NO: 2, immunogenic polypeptides thereof, and combinations thereof.

Embodiment 33 is the method of Embodiment 24, combination of Embodiment 25 or use of Embodiment 26, wherein the IVT repRNA comprises a polynucleotide encoding at least one antigenic protein having an amino acid sequence selected from the group consisting of SEQ ID NO: 1, SEQ ID NO: 2, and immunogenic polypeptides thereof.

Embodiment 34 is the method of Embodiment 24, combination of Embodiment 25 or use of Embodiment 26, wherein the adenovirus vector comprises a polynucleotide encoding at least one antigenic protein having an amino acid sequence selected from the group consisting of SEQ ID NO: 1, SEQ ID NO: 2, and immunogenic polypeptides thereof.

Embodiment 35 is the method of Embodiment 24, combination of Embodiment 25 or use of Embodiment 26, wherein the IVT repRNA is a Venezuelan equine encephalitis (VEE) virus-based repRNA.

Embodiment 36 is the method of Embodiment 24, combination of Embodiment 25 or use of Embodiment 26, wherein the adenovirus vector is an Ad26 vector or an Ad35 vector.

Embodiment 37 is a method of inducing an immune response in a human subject in need thereof, the method comprising:
  a. administering to the human subject a first composition comprising an immunologically effective amount of an in vitro transcribed (IVT) self-replicating RNA (repRNA) comprising a polynucleotide encoding non-structural proteins of Venezuelan Equine Encephalitis (VEE) Virus, and another polynucleotide encoding a first antigenic protein or an immunogenic polypeptide thereof, together with a pharmaceutically acceptable carrier, and
  b. administering to the subject a second composition comprising an immunologically effective amount of an Ad26 vector or an Ad35 vector comprising a second polynucleotide encoding a second antigenic protein or an immunogenic polypeptide thereof, together with a pharmaceutically acceptable carrier,
to thereby obtain an induced immune response in the human subject, wherein the first and second antigenic proteins share at least one antigenic determinant, and the first compositions is a priming composition and the second composition is a boosting composition.

Embodiment 38 is a combination for inducing an immune response in a human subject, comprising:
  a. a first composition comprising an immunologically effective amount of an in vitro transcribed (IVT) self-replicating RNA (repRNA) comprising a polynucleotide encoding non-structural proteins of Venezuelan Equine Encephalitis (VEE) Virus, and another polynucleotide encoding a first antigenic protein or an immunogenic polypeptide thereof, together with a pharmaceutically acceptable carrier, and
  b. a second composition comprising an immunologically effective amount of an Ad26 vector or an Ad35 vector comprising a second polynucleotide encoding a second antigenic protein or an immunogenic polypeptide thereof, together with a pharmaceutically acceptable carrier,
wherein the first and second antigenic proteins share at least one antigenic determinant, and the first compositions is a priming composition and the second composition is a boosting composition.

Embodiment 39 is a use of the combination of embodiment 38 for the preparation of a medicament for inducing an immune response in a human subject.

Embodiment 40 is the method of Embodiment 37, combination of Embodiment 38 or use of Embodiment 39, wherein the first or second antigenic protein or immunogenic polypeptide thereof is derived from a pathogen or a tumor.

Embodiment 41 is the method of Embodiment 38, combination of Embodiment 39 or use of Embodiment 40, wherein the first or second antigenic protein or immunogenic polypeptide thereof is derived from a virus.

Embodiment 42 is the method of Embodiment 37, combination of Embodiment 38 or use of Embodiment 39, wherein the first or second antigenic protein is derived from a RSV-preF protein, and wherein the first and second antigenic proteins are identical or substantially identical.

Embodiment 43 is the method of Embodiment 37, combination of Embodiment 38 or use of Embodiment 39, wherein the first and second antigenic proteins each independently comprise an amino acid sequence selected from the group consisting of SEQ ID NO: 1, SEQ ID NO: 2, immunogenic polypeptides thereof, and combinations thereof.

Embodiment 44 is the method of Embodiment 37, combination of Embodiment 38 or use of Embodiment 39, wherein the first composition comprises an immunologically effective amount of an IVT repRNA having the sequence of SEQ ID NO: 3, and the second composition comprises an immunologically effective amount of an Ad26 vector comprising a polynucleotide encoding an antigenic protein having the amino acid sequence of SEQ ID NO: 1.

Embodiment 45 is the method of any one of Embodiments 37-44, combination of any one of Embodiments 38-44 or use of any one of Embodiments 39-44, wherein the second composition is administered to the human subject 2 to 12 weeks, preferably 4 to 8 weeks, after the administration of the first composition.

Embodiment 46 is the method of any one of Embodiments 38 or 41-45, combination of any one of Embodiments 39 or 41-45 or use of any one of Embodiments 40-45, wherein the first composition is formulated as a lipo-nanoparticle formulation.

EXAMPLES

The following examples are offered to illustrate, but not to limit the claimed invention.

Example 1

An animal study was conducted with the goal of exploring the potential of homologous prime-boost immunizations with repRNA based vaccines encoding a model antigen. The model antigen that was used was the pre-fusion F protein from respiratory syncytial virus (RSV-preF). The study tested a dose-range of homologous vaccinations with an immunization interval of 4 weeks.

Animal Manipulations

The studies complied with all applicable sections of the Final Rules of the Animal Welfare Act regulations (9 CFR Parts 1, 2, and 3) and Guide for the Care and Use of Laboratory Animals—National Academy Press, Washington D.C. Eight Edition (the Guide).

A total of 30 (6 weeks old) female Balb/c mice were purchased from Jackson laboratories.

Vaccine Materials

Figure 1:
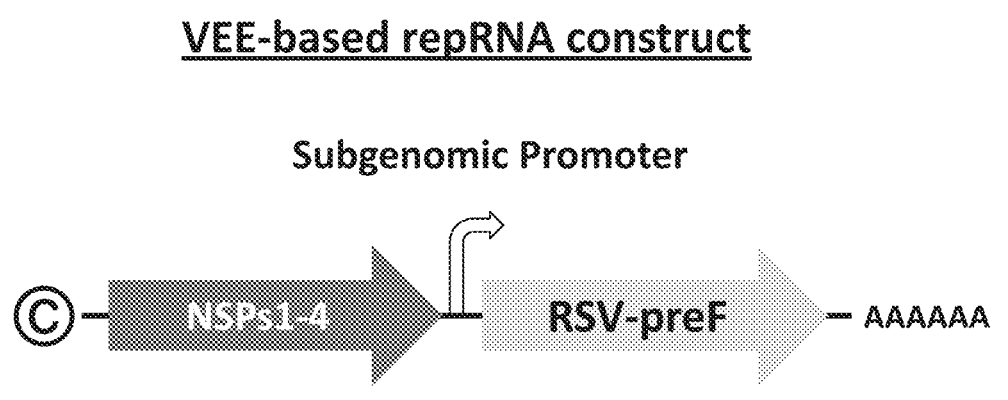

A schematic representation of the IVT repRNA vaccine vector that was used is depicted in FIG. 1. The IVT repRNA vector consisted of two open reading frames (ORFs), the first encoding the non-structural proteins (NSPs) of Venezuelan Equine Encephalitis (VEE) Virus, and the second encoding RSV-preF protein. The IVT repRNA vector was manufactured using in vitro transcription (IVT) and purification methods. Briefly, linear template DNA for T7 in vitro transcription was generated by digesting a replicon-bearing DNA plasmid 5' of the T7 promoter and 3' of the poly-A tail. The digested product was cleaned using a Zymo DNA Clean & Concentrator™-25 kit. IVT repRNA was generated using the Ambion MEGAscript® T7 transcription kit (Thermo) followed by an HPLC cleaning step using a GE CaptoCore 700 HiScreen column to remove buffer components, free NTPs and proteins. After cleaning, the IVT repRNA was capped by a post-transcriptional enzymatic capping reaction using a capping kit from Cellscript, after which the RNA was concentrated in a spin concentrator and buffer exchanged to a final concentration of 1-5 µg/µl. Formulation of repRNA into lipid nanoparticles (LNPs) was performed by a dilution process in ethanol. Cholesterol was obtained from Sigma-Aldrich, and 1,2-dioleoyl-3-trimethylammonium-propane (DOTAP), 1,2-distearoyl-sn-glycero-3-phosphocholine (DSPC) and 1,2-distearoyl-sn-glycero-3-phosphoethanolamine-N-[methoxy(polyethylene glycol)-2000] (DSPE-PEG) were obtained from Avanti Polar Lipids. Lipid components (in ethanol) at 48:40:10:2 molar percent of Cholesterol:DOTAP:DSPC:DSPE-PEG were mixed with repRNA in 10 mM Citrate buffer using a 8:1 N:P molar ratio (nitrogen on DOTAP to phosphate on RNA). After 1 h emulsification, particles were dialyzed against PBS. Prior in vivo injections, particles were further diluted to required RNA concentration in PBS.

The IVT repRNA expressed VEE viral replicases and an antigenic RSV-preF protein having the amino acid sequence of SEQ ID NO:2. The template DNA sequence used to generate the IVT repRNA had the nucleotide sequence of SEQ ID NO:3.

Vaccination and Experimental Design

Balb/c mice were vaccinated with a homologous prime-boost regimen using repRNA (see Table 1 and FIG. 2 for grouping and experimental design). Prior to immunization, each mouse was anesthetized with 1-4% isoflurane in oxygen using a rodent anesthesia machine, and received intramuscular (IM) injections of lipid-nanoparticle (LNP)-formulated repRNA (50 µL). Priming and boosting doses were given 4 weeks apart (FIG. 2).

Whole blood without anticoagulant was processed for serum. Each serum was assayed in a RSV preF-specific ELISA.

TABLE 1

Experimental grouping of animals in homologous repRNA immunization study to explore humoral responses

| Animal Groups (Balb/c) | Vaccine | Vehicle | Immunizations (weeks) | Dose (µg) | Animals/ group |
|---|---|---|---|---|---|
| 1-4 | repRNA-RSV-preF | LNP | 0, 4 | 5, 1, 0.4, 0.02 | 6 |
| 5 | None | LNP | 0, 4 | 0 | 6 |

Anti-RSV-F IgG ELISA

RSV-F-specific humoral responses were determined at 28 and 42 days after immunization by a modified enzyme-linked immunosorbent assay (ELISA), as previously described in Krarup et al. (A highly stable prefusion RSV F vaccine derived from structural analysis of the fusion mechanism. Nat. Commun. 6:8143).

Briefly, MaxiSorp polystyrene 96-well plates (NUNC) were coated with human anti-RSV F monoclonal antibody (Synagis) overnight at 4° C. at a concentration of 1 µg/ml in PBS. The next day, plates were washed with PBST washing buffer (PBS, 0.05% Tween) and blocked in PBS with 1% bovine serum albumin followed by incubation with a stabilized pre-fusion F protein (0.25 μg/ml in PBST), which was captured by the immobilized anti-RSV F antibodies.

Figure 3:
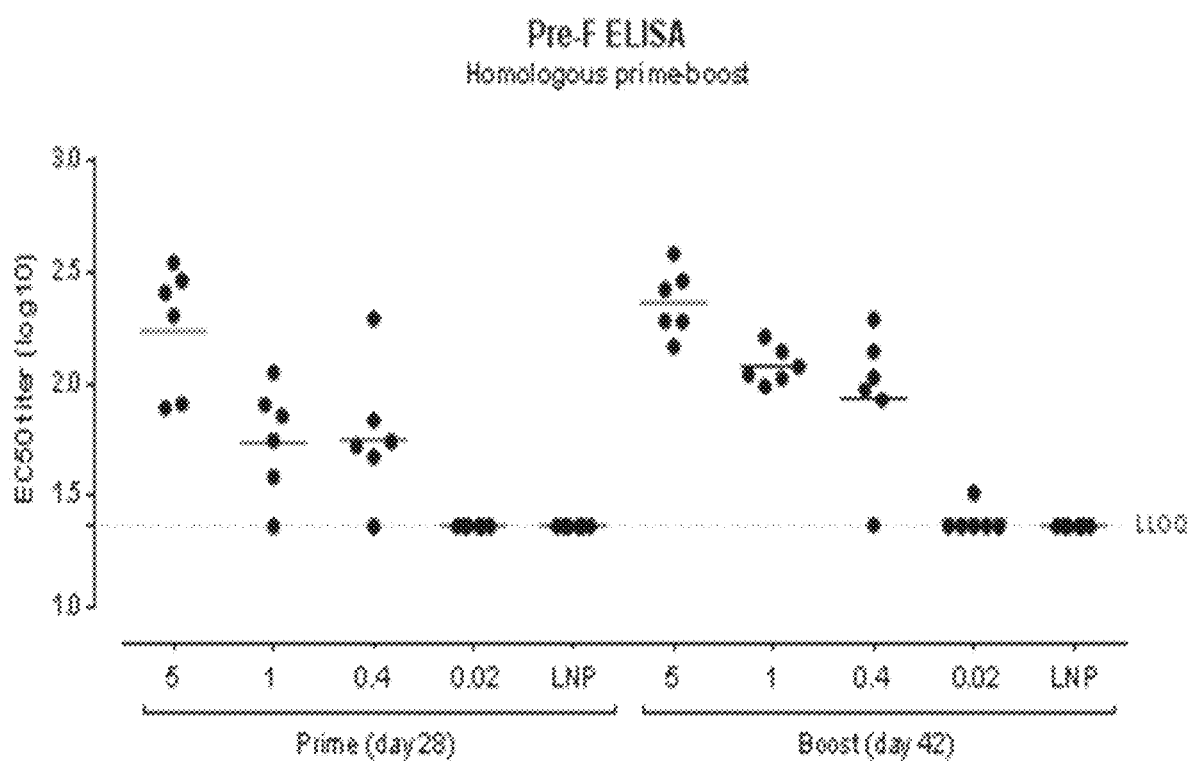
FIG. 3 shows the RSV-preF protein specific humoral immune responses from a homologous IVT repRNA immunization study, as assessed by ELISA.

Serum samples were diluted in PBST with 1% bovine serum albumin and incubated with goat-anti-mouse-IgG-HRP conjugate from Bio-Rad (1/5000 dilution in PBST), and the samples were then incubated in the wells to allow for detection of RSV-F specific murine IgG. OPD substrate was used for detection. All incubations were performed at room temperature for 1 h. After each step, the plates were washed three times with PBST. Results from the ELISA assay are shown in FIG. 3. Prime immunizations with doses of 0.4 μg or higher resulted in humoral immune responses having detectable IgG titers, and homologous boosting resulted in only a marginal increase in IgG titers (cross-dose).

Example 2

To explore the cellular responses after a homologous repRNA boost, an animal study was conducted in which splenocytes were tested in an ELISPOT using an RSV-F specific peptide.

Animal Manipulations

The studies complied with all applicable sections of the Final Rules of the Animal Welfare Act regulations (9 CFR Parts 1, 2, and 3) and *Guide for the Care and Use of Laboratory Animals—National Academy Press, Washington D.C. Eight Edition* (the Guide).

Female Balb/c mice (6 weeks old) were purchased from Jackson laboratories.

Vaccine Materials

IVT repRNA was generated and formulated as described in Example 1.

Vaccination and Experimental Design

Figure 4:
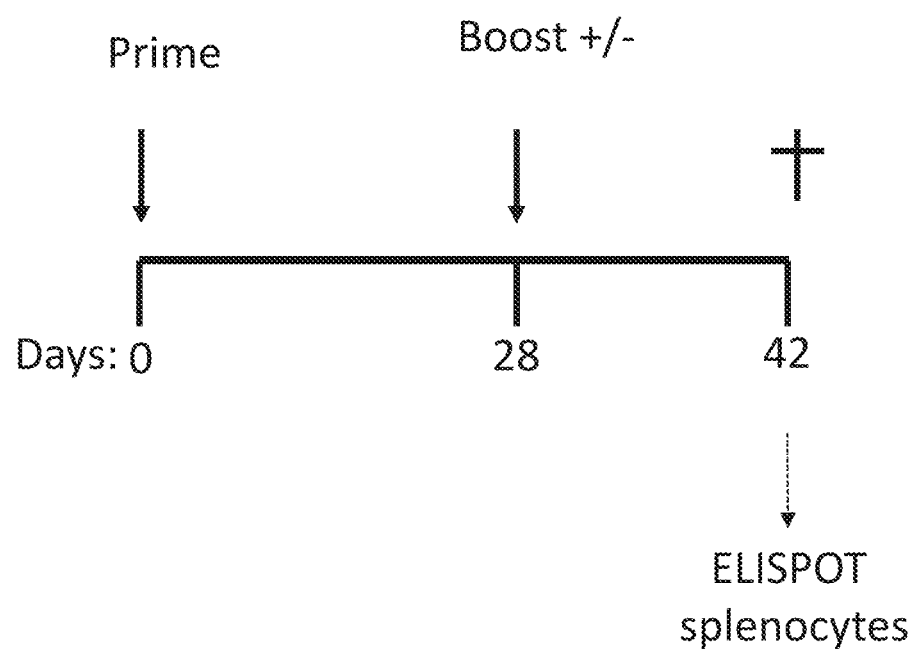
FIG. 4 shows an experimental design of a homologous IVT repRNA immunization study in which analysis was carried out by ELISPOT.

Balb/c mice were vaccinated with a homologous prime-boost regimen using repRNA (see Table 2 and FIG. 4 for grouping and experimental design). Prior to immunization, each mouse was anesthetized with 1-4% isoflurane in oxygen using a rodent anesthesia machine, and received intramuscular (IM) injections of lipid-nanoparticle (LNP)-formulated repRNA (50 μL). Priming and boosting doses were given 4 weeks apart (FIG. 4).

After 6 weeks, all mice were sacrificed to obtain splenocytes for testing in an IFN-g ELISPOT assay using the RSV-F specific CTL peptide KYKNAVTEL assay.

TABLE 2

Experimental grouping of animals in homologous repRNA immunization (i.m.) study to explore cellular responses

| Group | Prime | Boost 1 (wk 4) | Dose repRNA (μg) | Mice/group | Vaccination weeks |
|---|---|---|---|---|---|
| 1 | PBS | — |   | 4 | 0, 6† |
| 2 | repRNA | — | 1 | 10 | 0, 6† |
| 3 | repRNA | repRNA | 1 | 10 | 0, 4, 6† |

IFN-G ELISPOT Assay

Figure 5:
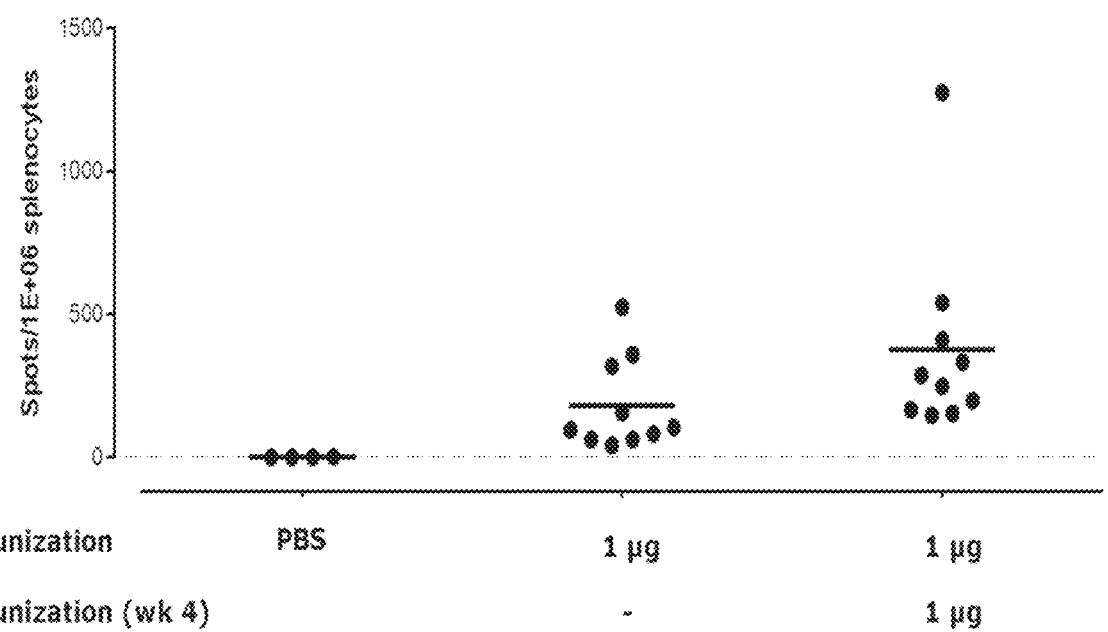
FIG. 5 shows the RSV-preF protein specific T-cell responses from a homologous IVT repRNA immunization study, as assessed by an IFN-γ ELISPOT assay using PBMCs and the CTL-activating peptide KYKNAVTEL from RSV-F.

RSV-F-specific cellular immune responses using splenocytes were determined at time point described in FIG. 4 by interferon gamma Enzyme-linked immunospot assay (ELISPOT) using IFNγ ELISPOT kit for mouse cells from BD. Briefly, 500,000 splenocytes per well were stimulated overnight with the CTL activating RSV-F peptide (KYKNAVTEL) at a final concentration of 1 μg/ml. Subsequently, spots were developed following the kit manufacturer instructions. The results of the ELISPOT assay are shown in FIG. 5 and indicate that cellular responses were only marginally increased (not statistically significant) after a boost.

Example 3

Due to the absence of boosting potential of the IVT repRNA vaccine in a homologous prime-boost regimen, an animal study was conducted with the objective of exploring the potential of heterologous prime-boost immunizations with repRNA-based vaccines in combination with Adeno-based vaccines, both encoding a model antigen. In particular, the study tested two heterologous vaccinations, comprising repRNA and Ad26-RSV-F with an immunization interval of 4 weeks, to determine whether the heterologous prime-boost vaccination would improve humoral or cellular immune responses compared to the homologous repRNA vaccination of Examples 1 and 2.

Animal Manipulations

These studies complied with all applicable sections of the Final Rules of the Animal Welfare Act regulations (9 CFR Parts 1, 2, and 3) and Guide for the Care and Use of Laboratory Animals—National Academy Press, Washington D.C. Eight Edition (the Guide).

A total of 36 (6 weeks old) female Balb/c mice were purchased from Jackson laboratories Vaccine Materials IVT repRNA was generated and formulated as described in Example 1.

The recombinant adenovirus vector, which was a purified E1/E3-deleted replication-deficient recombinant adenovirus type 26 vaccine vector (Ad26) containing the RSV-F gene inserted at the E1 position, was manufactured by Janssen R&D. The vector was rescued in PER.C6® cells, plaque-purified, up-scaled and then purified by a two-step CsCl banding procedure, and subsequently formulated in a TRIS-based formulation buffer and stored below −65° C.

The recombinant adenovirus vector expressed RSV-F derived from the RSV-A2 strain. The expressed RSV-F protein had the amino acid sequence of SEQ ID NO1.

The vaccine materials were stored at −80° C. in a controlled temperature freezer.

Vaccination and Experimental Design

Figure 6:
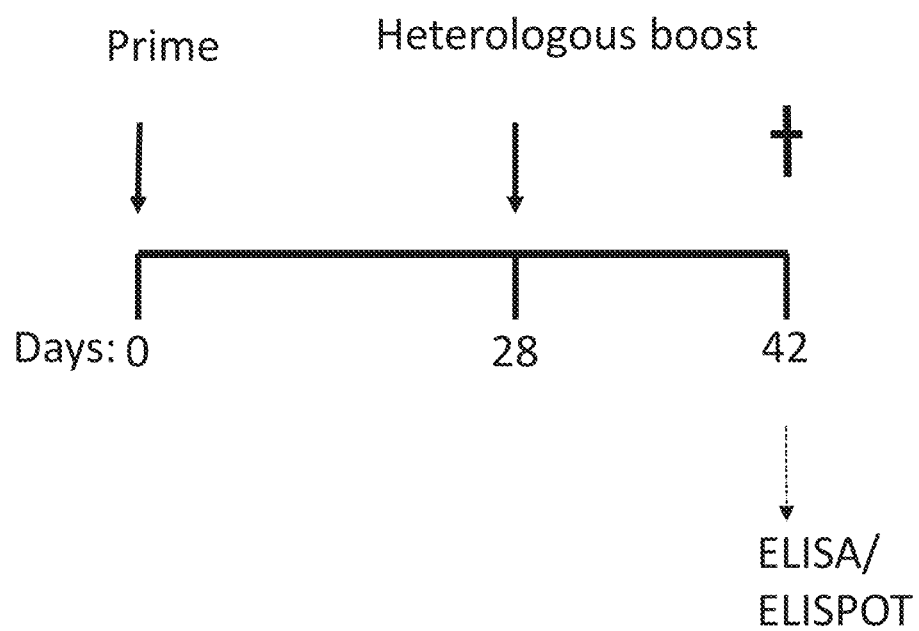
FIG. 6 shows an experimental design of a heterologous IVT repRNA and adenovirus vector immunization study in which analysis was carried out by ELISA and ELISPOT.

Balb/c mice were vaccinated with a heterologous prime-boost regimen using repRNA and Adeno vector (see Table 3 and FIG. 6 for grouping and experimental design). Prior to immunization, each mouse was anesthetized and received intramuscular (IM) injections of Adeno vector or lipid-nanoparticle (LNP) formulated repRNA (as described in Example 1) into the hind thighs. Priming and boosting doses were given 4 weeks apart (FIG. 6).

The animal study was performed to explore whether a heterologous prime-boost vaccination using repRNA and Ad26-RSV-F would improve humoral or cellular immune responses (see Table 3 for grouping of mice and FIG. 6 for experimental design) in contrast to homologous repRNA vaccination, as demonstrated by Examples 1 and 2. All immunizations were intra-muscular. Three control groups of mice received prime-only immunizations (i.m.) with either PBS, LNP-formulated repRNA (1 µg), or Ad26-RSV-F ($1\times10^9$ vp). The potential of heterologous prime-boost immunizations was tested in two additional groups of mice. One group of 8 mice was primed with LNP-formulated repRNA (1 ug) and 4 weeks later boosted with Ad26-RSV-F ($1\times10^9$ vp). The other group of 8 mice was primed with Ad26-RSV-F ($1\times10^9$ VPs) followed by a boost after 4 weeks with LNP-formulated repRNA (1 µg).

TABLE 3

Experimental grouping of animals in heterologous immunization study

| Group | Prime | Boost 1 (week 4) | Dose Adeno (VPs) | Dose repRNA (µg) | Mice/ group | Vaccination weeks |
|---|---|---|---|---|---|---|
| 1 | PBS | PBS | — | — | 4 | 0, 6+ |
| 2 | repRNA | — | — | 1 | 8 | 0, 6+ |
| 3 | adenovirus | — | $10^9$ | — | 8 | 0, 6+ |
| 4 | repRNA | adenovirus | $10^9$ | 1 | 8 | 0, 4, 6+ |
| 5 | adenovirus | repRNA | $10^9$ | 1 | 8 | 0, 4, 6+ |

Anti-RSV-F IgG ELISA

Figure 7:
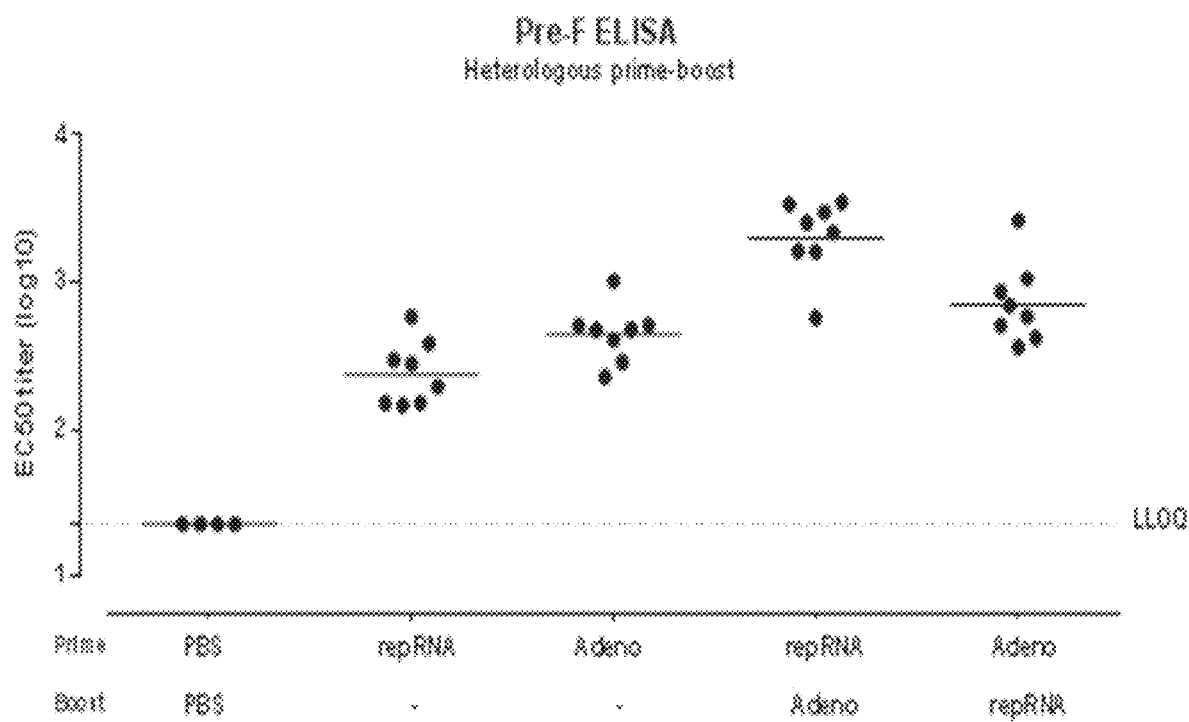
FIG. 7 shows the RSV-preF protein specific humoral immune responses from a heterologous IVT repRNA and adenovirus vector immunization study, as assessed by ELISA.

RSV-F-specific humoral responses were determined at 42 days after immunization by anti-RSV-F IgG ELISA analysis as described in Example 1. Results from the ELISA assay are shown in FIG. 7. Heterologous prime-boost immunizations with repRNA and adenovirus vector resulted in humoral immune responses having increased IgG titers compared to homologous immunizations with repRNA or adenovirus vector.

IFN-γ ELISPOT Assay

Figure 8:
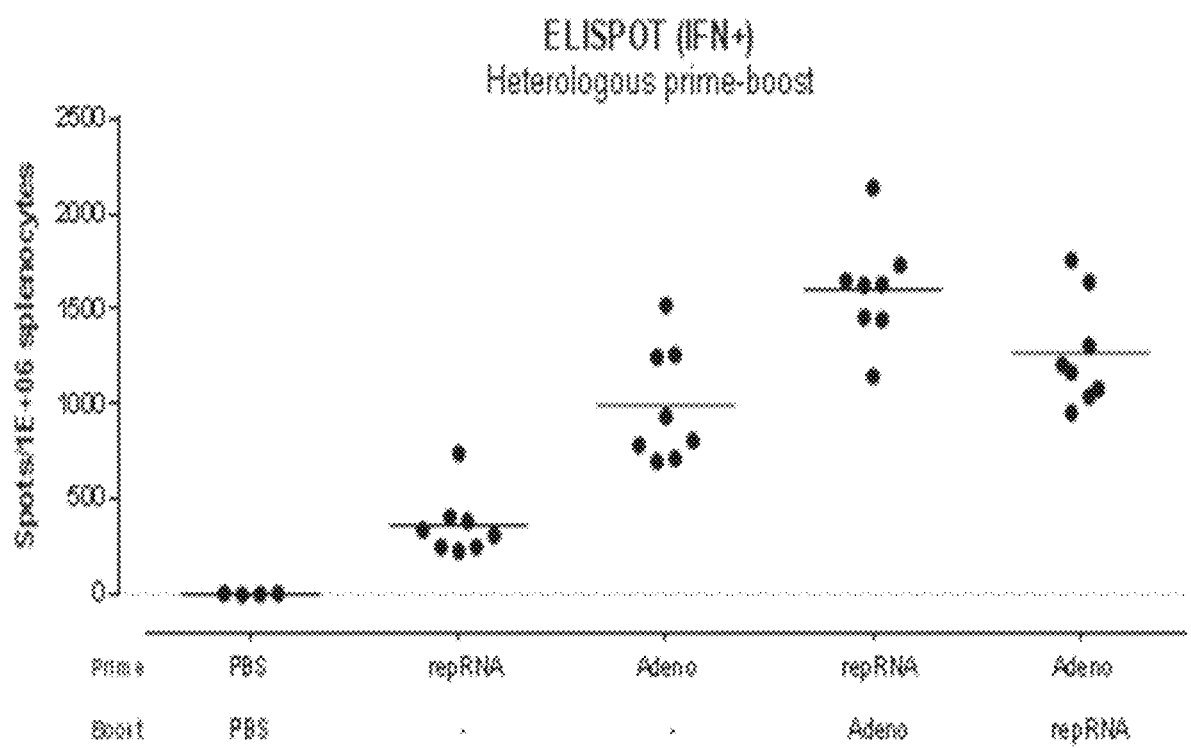
FIG. 8 shows the RSV-preF protein specific T-cell responses from a heterologous IVT repRNA and adenovirus vector immunization study, as assessed by an IFN-γ ELISPOT assay using splenocytes.

RSV-F-specific cellular (splenocytes) immune responses were determined at 42 days after immunization by interferon gamma ELISPOT analysis as described in Example 2. Results of the ELISPOT assay are shown in FIG. 8. Heterologous prime-boost immunizations with repRNA and adenovirus vector resulted in increased cellular immune responses compared to prime-only immunizations with repRNA or adenovirus vector.

In summary, the study demonstrated that increased humoral and cellular immune responses were induced by immunization with heterologous vaccines of repRNA and adenovirus vectors as compared to homologous immunizations with repRNA or adenovirus vector only.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of inducing an immune response in a human subject in need thereof, the method comprising:
   a. administering to the human subject a first composition comprising an immunologically effective amount of an in vitro transcribed (IVT) self-replicating RNA (repRNA) comprising a first polynucleotide encoding a first antigenic protein or an immunogenic polypeptide thereof, together with a pharmaceutically acceptable carrier, wherein the IVT repRNA is formulated into a non-virion particle, and
   b. administering to the subject a second composition comprising an immunologically effective amount of a recombinant human adenovirus serotype 26 (Ad26) vector or a recombinant human adenovirus serotype 35 (Ad35) vector comprising a second polynucleotide encoding a second antigenic protein or an immunogenic polypeptide thereof, together with a pharmaceutically acceptable carrier,
   to thereby obtain an induced immune response in the human subject, wherein the first and second antigenic proteins share at least one antigenic determinant, and one of the compositions is a priming composition and the other composition is a boosting composition.

2. The method according to claim 1, wherein the composition comprising the IVT repRNA is the priming composition and the composition comprising the adenovirus vector is the boosting composition.

3. The method according to claim 1, wherein the composition comprising the adenovirus vector is the priming composition and the composition comprising the IVT repRNA is the boosting composition.

4. The method according to claim 1, wherein the induced immune response comprises an induced antibody immune response against the at least one antigenic determinant shared by the first and second antigenic proteins in the human subject.

5. The method according to claim 1, wherein the induced immune response comprises an induced cellular immune response against the at least one antigenic determinant shared by the first and second antigenic proteins in the human subject.

6. The method according claim 1, wherein the induced immune response provides a protective immunity to the human subject against a disease related to at least one of the first and second antigenic proteins.

7. The method according to claim 1, wherein the IVT repRNA is a Venezuelan equine encephalitis (VEE) virus-based repRNA.

8. The method according to claim 1, wherein the boosting composition is administered 1-52 weeks after the priming composition is administered.

9. The method according to claim 1, wherein the boosting composition is administered at least 1 week after the priming composition is administered.

10. The method according to claim 1, wherein the first and second antigenic proteins are derived from a pathogen or a tumor.

11. The method according to claim 1, wherein the first or second antigenic protein is derived from a virus.

12. The method according to claim 1, wherein the first and second antigenic proteins are identical or substantially identical.

13. An immunogenic composition for inducing an immune response in a human subject, comprising:
   a. a first composition comprising an immunologically effective amount of an IVT repRNA comprising a first polynucleotide encoding a first antigenic protein or an immunogenic polypeptide thereof, together with a pharmaceutically acceptable carrier, wherein the IVT repRNA is formulated into a non-virion particle, and
   b. a second composition comprising an immunologically effective amount of a recombinant human adenovirus serotype 26 (Ad26) vector or a recombinant human adenovirus serotype 35 (Ad35) vector comprising a second polynucleotide encoding a second antigenic protein or an immunogenic polypeptide thereof, together with a pharmaceutically acceptable carrier, wherein the first and second antigenic proteins share at least one antigenic determinant, and one of the compositions is a priming composition and the other composition is a boosting composition.

14. The immunogenic composition of claim 13, wherein the first composition comprising the IVT repRNA is the priming composition and the second composition comprising the adenovirus vector is the boosting composition.

15. The immunogenic composition of claim 13, wherein the second composition comprising the adenovirus vector is the priming composition and the first composition comprising the IVT repRNA is the boosting composition.

16. The immunogenic composition of claim 13, wherein the first or second antigenic protein or immunogenic polypeptide thereof is derived from a pathogen or a tumor.

17. The immunogenic composition of claim 13, wherein the first or second antigenic protein or immunogenic polypeptide thereof is derived from a virus.

18. The immunogenic composition of claim 13, wherein the first and second antigenic proteins are identical or substantially identical.

19. The immunogenic composition of claim 13, wherein the IVT repRNA is a VEE virus-based repRNA.

20. The method of claim 1, wherein the non-virion particle is a lipid nanoparticle (LNP).

21. The immunogenic composition of claim 13, wherein the non-virion particle is a lipid nanoparticle (LNP).

* * * * *